United States Patent [19]
Ohtsuka et al.

[11] Patent Number: 5,631,115
[45] Date of Patent: May 20, 1997

[54] LOOPED, HAIRPIN RIBOZYME

[75] Inventors: Eiko Ohtsuka, Sapporo; Makoto Koizumi, Tokyo, both of Japan

[73] Assignee: Sankyo Company, Limited, Tokyo, Japan

[21] Appl. No.: 367,175

[22] PCT Filed: Jul. 2, 1993

[86] PCT No.: PCT/JP93/00907

§ 371 Date: Dec. 29, 1994

§ 102(e) Date: Dec. 29, 1994

[87] PCT Pub. No.: WO94/01549

PCT Pub. Date: Jan. 20, 1994

[30] Foreign Application Priority Data

Jul. 2, 1992 [JP] Japan .................................. 4-175706
Sep. 4, 1992 [JP] Japan .................................. 4-236916

[51] Int. Cl.$^6$ .......................... C12P 19/34; C07H 21/00
[52] U.S. Cl. .................................. 435/91.31; 536/24.5
[58] Field of Search .......................... 435/91.31; 536/24.5

[56] References Cited

PUBLICATIONS

Barinaga Ribozymes: Killing the messenger Science 262 1512–1514 1993.
Stull et al. Antigene, ribozyme and aptamer nucleic acid drugs: progress and prospects Pharmaceutical Res. 12 465–483 1995.
Gerry A. Prody, et al., "Autolytic Processing of Dimeric Plant Virus Satellite RNA", *Science*, 231, 1577–1580 (1986).
Cheryl J. Hutchins et al., "Self–cleavage of plus and minus RNA transcripts of avocado sunblotch viroid", *Nucleic Acids Research*, 14, 3627–3640 (1986).
Olke C. Uhlenbeck, "A small catalytic oligoribonecleotide", *Nature*, 328, 596–600 (1987).
Lloyd M. Epstein et al., "Self–Cleaving Transcripts of Satellite DNA from the Newt", *Cell*, 48, 535–543 (1987).
Makoto Koizumi et al., "Construction of a series of several self–cleaving RNA duplexes using synthetic 21–mers", *FEBS Letters*, 228, 228–230 (1988).
Makoto Koizumi et al., "Design of RNA enzymes distinguishing a single base mutation in RNA", *Nucleic Acids Research*, 17, 7059–7071 (1989).
Jamal M. Buzayan et al., "Non–enzymatic cleavage and ligation of RNAs complementary to a plant virus satellite RNA", *Nature*, 323, 349–353, (1986).
Arnold Hampel et al., "RNA Catalytic properties of the Minimum (–) sTRSV Sequence", *Biochemistry*, 28, 4929–4933 (1989).
Akira Sekiguchi et al., "Mutagenesis and self–ligation of the self–cleavage domain of the satellite RNA minus strand of tobacco ringspot virus and its binding to polyamines", *Nucleic Acids Research*, 19, 6833–6838 (1991).

George Slim et al, "Configurationally defined phosphorothioate–containing oligoribonucleotides in the study of the mechanism of cleavage of hammerhead ribozymes", *Nucleic Acids Research*, 19, 1183–1188 (1991).
Craig Tuerk et al, "CUUCGG Hairpins: Extraordinarily Stable RNA Structures Associated With Various Biochemical Processes", *Proc. Natl. Acad. Sci. USA*, 85, 1364–1368, Mar. 1988.
Chaejoon Cheong et al, "Solution Structure of an Unusually Stable RNA Hairpin, 5'GGAC(UUCG)GUCC", *Nature*, 346, 680–682 (1990).
Burke et al., "Genes & Development", vol. 6, (1992), pp. 129–134.
John M. Burke et al, "Novel guanosine requirement for catalysis by the hairpin ribozyme", *Nature*, vol. 354, Nov. 28, 1991, pp. 320–322.
Ignacio Tinoco et al, "Solution structure of an unusually stable RNA hairpin 5'GGAC(UUCG)GUCC", *Nature*, vol. 346, Aug. 16, 1990, pp. 680–682.
Sekiguchi et al, "Mutagenesis and self–ligation of the self–cleavage domain of the satellite RNA minus strand of tobacco ringspot virus and its binding to polamines", *Nucleic Acids Res.*, vol. 19, (1991) pp. 6833–6838.
Ohtsuka et al, "Ribozymes designed to inhibit transformation of NIH3T3 cells by activated c–Ha–ras gene", GENE (Amsterdam), vol. 117, No. 2, (1992), pp. 179–184.

*Primary Examiner*—James Ketter
*Assistant Examiner*—John S. Brusca
*Attorney, Agent, or Firm*—Frishauf, Holtz, Goodman, Langer & Chick, P.C.

[57] ABSTRACT

A polyribonucleotide having a thermodynamically stable loop structure and ribozyme activity and a DNA that codes for the polyribonucleotide. The polyribonucleotide has the following structure

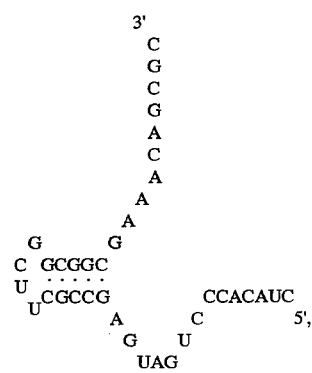

Direct administration of the ribozyme polyribonucleotide of the present invention into the body of a patient enables a target polyribonucleotide in the body to be efficiently cleaved, thereby allowing it to be used as an anti–AIDS drug.

22 Claims, 5 Drawing Sheets

FIG. 3

```
CGAT  CTACACCCTGATGAGCCGCTTCGGCGGCGAAACAGCGC G
  TA  GATGTGGGACTACTCGGCGAAGCCGCCGCTTTGTCGCG  CAGCT
Cla I └────── ribozyme polyribonucleotide gene ──────┘ Sal I
```

LOOPED, HAIRPIN RIBOZYME

TECHNICAL FIELD

The present invention relates to a polyribonucleotide having a thermodynamically stable loop structure and ribozyme activity, a DNA that codes for said polyribonucleotide, an expression vector containing said DNA, a host cell transfected with said expression vector, and a process for cleaving a specific site of a substrate polyribonucleotide by said polyribonucleotide having ribozyme activity.

BACKGROUND ART

The (+) chain of satellite RNA of tobacco ringspot virus and the (+) chain and (−) chain of avocado sunblotch viroid are cleaved by their own catalytic activity in the presence of $Mg^{2+}$ (Science 231, 1577–1580 (1986)). The RNA structure necessary for this cleavage activity has been determined and named as Hammerhead ribozyme (Nucleic Acids Res. 14, 3627–3640 (1986)). The nucleotide sequences in the vicinity of the cleavage sites of these RNA possesses common sequences, and the secondary structure of these RNA was predicted from this common sequences. Uhlenbeck designed a short chain RNA fragment of 19 mer based on these common sequences, and indicated that said fragment catalytically cleaves RNA of 24 mer (Nature, 328, 596–600 (1987)).

In addition, besides viroid and vital satellite RNA, the transcript of newt satellite DNA is also reported to have ribozyme nucleotide sequences (Cell, 48, 535–543, (1987)).

The inventors of the present invention chemically synthesized two types of 21 mer RNA having nucleotide sequences in the vicinity of the cleavage site of this newt satellite DNA transcript. When one of the RNA was added to the other, a cleavage reaction was found to occur at the same site as that in nature (FEBS Lett., 228, 228–230, (1988)). In addition, based on this result, the inventors of the present invention found a process for cleaving other RNA or polyribonucleotide molecules using ribozyme (Nucleic Acids Res., 17, 7059–7071, (1989)).

On the other hand, a cleavage reaction was also caused on the (−) chain of the satellite RNA of tobacco ringspot virus, and that cleavage has been determined to occur at a specific site (Nature 323, 349–353 (1986)). In addition, the minimum region of RNA necessary for this cleavage has also been recently clarified (Biochemistry, 28, 4929–4933 (1989)). RNA having this catalytic activity is composed of 50 nucleotides, and a model having a hairpin loop structure within this RNA has been advocated. This RNA has been given the name hairpin ribozyme. The present inventors and other research groups converted the nucleotides of this hairpin ribozyme to other nucleotides, and used those results to identify several nucleotides that are important in the cleavage reaction (Nature 354, 320–322 (1991), Nucleic Acids Res. 19, 6833–6838 (1991)). Further, the group of Burke et al. has recently identified the base sequence which is important in the cleavage reaction and ligation reaction of hairpin ribozyme by in vitro selection method using DNA having random variation and PCR (polymerase chain reaction) (Gene & Development 6, 129–134 (1992)). The present inventors have determined that catalytic reaction proceeds even for RNA deleting the hairpin loop portion (Nucleic Acids Res. 19, 6833–6838 (1991)).

In addition, progress in RNA synthesis techniques in recent years has made it possible to obtain RNA in large volume, and thus, researches on higher-order structures of RNA and its physicochemical properties are increasingly made. Bacteriophage $T_4$ mRNA and $E.\ coli$ 16S ribosomal RNA contain 5'CUUCGG3' sequences in high frequency, and it has been determined that the hairpin loop structure formed by this sequence is thermodynamically stable (Pro. Natl. Acad. Sci. USA, 85, 1364–1368, (1988): Nature, 346, 680–682, (1990)).

The present inventors prepared a polyribonucleotide wherein the nucleotide sequence of a hairpin loop which exists at one location within the ribozyme is the above-mentioned thermodynamically stable 5'CUUCGG3' sequence, and they found that this polyribonucleotide possesses high ribozyme cleavage activity and accomplished the present invention. As a result of having a thermodynamically stable hairpin loop structure, the ribozyme in the present invention is expected to efficiently cleave target polyribonucleotides in the living body.

SUMMARY OF THE INVENTION

The present invention relates to:

(1) a polyribonucleotide represented by the following general formula (I):

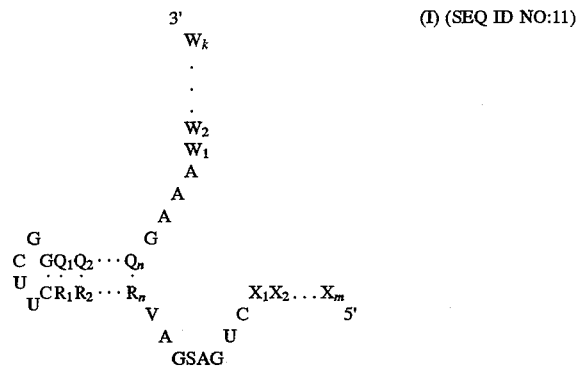
(I) (SEQ ID NO:11)

wherein,

U represents an uracil nucleotide, C a cytosine nucleotide, A an adenine nucleotide, and G a guanine nucleotide.

S represents either an uracil nucleotide, adenine nucleotide, cytosine nucleotide or guanine nucleotide, V represents either an uracil nucleotide, adenine nucleotide, cytosine nucleotide or guanine nucleotide, $Q_1$ through $Q_n$ may be the same or different from one another and represent either a cytosine nucleotide or guanine nucleotide, $R_1$ through $R_n$ represent nucleotides that are respectively complementary to $Q_1$ through $Q_n$, $W_1$ through $W_k$ may be the same or different from one another and represent either an uracil nucleotide, adenine nucleotide, cytosine nucleotide or guanine nucleotide, $X_1$ through $X_m$ may be the same or different from one another and represent either an uracil nucleotide, adenine nucleotide, cytosine nucleotide or guanine nucleotide, and k, m and n may be the same or different from one another and represent an integer from 1 to 10;

(2) a polyribonucleotide in general formula (I) set forth in (1) wherein $W_1$ is a cytosine nucleotide or a guanine nucleotide:

(3) a polyribonucleotide represented by the following general formula (II):

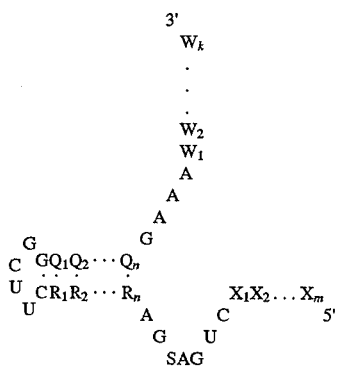

(II) (SEQ ID NO:12)

wherein,
represents an uracil nucleotide, C a cytosine nucleotide, A an adenine nucleotide, and G a guanine nucleotide, S represents either an uracil nucleotide, adenine nucleotide, cytosine nucleotide or guanine nucleotide, $Q_1$ through $Q_n$ may be the same or different from one another and represent either a cytosine nucleotide or guanine nucleotide, $R_1$ through $R_n$ represent nucleotides that are respectively complementary to $Q_1$ through $Q_n$, $W_1$ through $W_k$ may be the same or different from one another and represent either an uracil nucleotide, adenine nucleotide, cytosine nucleotide or guanine nucleotide, $X_1$ through $X_m$ may be the same or different from one another and represent either an uracil nucleotide, adenine nucleotide, cytosine nucleotide or guanine nucleotide, and k, m and n may be the same or different from one another and represent an integer from 1 to 10);

(4) a polyribonucleotide of general formula (II) set forth in (3) wherein $W_1$ is a cytosine nucleotide or a guanine nucleotide;

(5) a DNA that codes for the polyribonucleotides set forth in (1), (2), (3) or (4);

(6) a recombinant vector that includes the DNA set forth in (5);

(7) a host cell transfected with the recombinant vector set forth in (6);

(8) a process for cleaving polyribonucleotide β at the site indicated with the arrow in the formula using polyribonucleotide α in the following general formula (III):

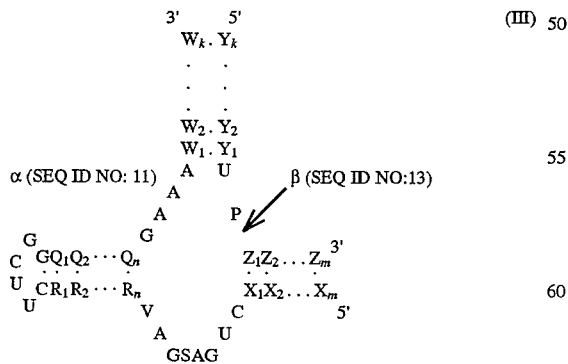

(III)

wherein,
U represents an uracil nucleotide, C a cytosine nucleotide, A an adenine nucleotide, and G a guanine nucleotide, S represents either an uracil nucleotide, adenine nucleotide, cytosine nucleotide or guanine nucleotide, V represents either an uracil nucleotide, adenine nucleotide, cytosine nucleotide or guanine nucleotide, $Q_1$ through $Q_n$ may be the same or different from one another and represent either a cytosine nucleotide or guanine nucleotide, $R_1$ through $R_n$ represent nucleotides that are respectively complementary to $Q_1$ through $Q_n$, $W_1$ through $W_k$ may be the same or different from one another and represent either an uracil nucleotide, adenine nucleotide, cytosine nucleotide or guanine nucleotide, $X_1$ through $X_m$ may be the same or different from one another and represent either an uracil nucleotide, adenine nucleotide, cytosine nucleotide or guanine nucleotide, P represents either an uracil nucleotide, adenine nucleotide or cytosine nucleotide, $Y_1$ through $Y_k$ represent nucleotides respectively complementary to $W_1$ through $W_k$, $Z_1$ through $Z_m$ represent nucleotides respectively complementary to $X_1$ through $X_m$, and k, m and n may be the same or different from one another and represent an integer from 1 to 10);

(9) a process for cleaving polyribonucleotide β in general formula (III) set forth in (8), wherein $Y_1$ is a guanine nucleotide or cytosine nucleotide complementary to $W_1$, using polyribonucleotide α, wherein $W_1$ is a cytosine nucleotide or guanine nucleotide;

(10) a process for cleaving polyribonucleodide δ at the site indicated with an arrow in the formula using polyribonucleotide γ in the following general formula (IV):

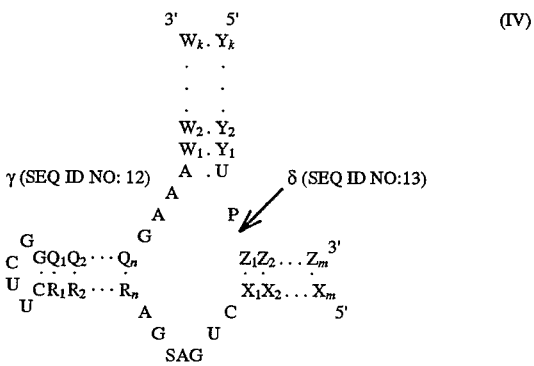

(IV)

wherein,
U represents an uracil nucleotide, C a cytosine nucleotide, A an adenine nucleotide, and G a guanine nucleotide, S represents either an uracil nucleotide, adenine nucleotide, cytosine nucleotide or guanine nucleotide, $Q_1$ through $Q_n$ may be the same or different from one another and represent either a cytosine nucleotide or guanine nucleotide, $R_1$ through $R_n$ represent nucleotides that are respectively complementary to $Q_1$ through $Q_n$, $W_1$ through $W_k$ may be the same or different from one another and represent either an uracil nucleotide, adenine nucleotide, cytosine nucleotide or guanine nucleotide, $X_1$ through $X_m$ may be the same or different from one another and represent either an uracil nucleotide, adenine nucleotide, cytosine nucleotide or guanine nucleotide, P represents either an uracil nucleotide, adenine nucleotide or cytosine nucleotide, $$
\begin{array}{llllllll}
 & & & 3' & \downarrow & & & \text{(VI)} \\
 & & & |\ 5' & & & & \\
 & G & AUA & AC & A\ | & PGLV & & \zeta\ (\text{SEQ ID NO:15}) \\
C & GQ_1Q_2\ldots Q_n\ GU & UU & CUGGU & Y_4Y_3Y_2Y_1 & & Z_1Z_2\ldots Z_m\text{-}3' \\
U & CR_1R_2\ldots R_n\ CA & AG & GACCAW_4W_3W_2W_1 & & & X_1X_2\ldots X_m\text{-}5' \\
 & U & A & A & A & AAGS & & \\
 & & & & & \epsilon\ (\text{SEQ ID NO:14}) & &
\end{array}
$$

$Y_1$ through $Y_k$ represent nucleotides respectively complementary to $W_1$ through $W_k$, $Z_1$ through $Z_m$ represent nucleotides respectively complementary to $X_1$ through $X_m$, and k, m and n may be the same or different from one another and represent an integer from 1 to 10); and

(11) a process for cleaving polyribonucleotide δ in general formula (IV) set forth in (10), wherein $Y_1$ is a guanine nucleotide or cytosine nucleotide complementary to $W_1$, using polyribonucleotide γ, wherein $W_1$ is a cytosine nucleotide or guanine nucleotide.

In addition, the present invention also relates to:

(12) a polyribonucleotide comprising in its molecule the nucleotide sequence represented by the following general formula (V):

$$
\begin{array}{lllllll}
 & & & & 3' & & \\
 & & & & | & & \\
 & G & AUA & AC & A & & \\
C & GQ_1Q_2\ldots Q_n\ GU & UU & CUGGU & & & \\
U & CR_1R_2\ldots R_n\ CA & AG & GACCAW_4W_3W_2W_1 & & X_1X_2\ldots X_m\text{-}5' \\
 & U & A & A & A & AAGS &
\end{array}
$$

(V) (SEQ ID NO:14)

wherein,

U represents an uracil nucleotide, C a cytosine nucleotide, A an adenine nucleotide, and G a guanine nucleotide, S represents either an adenine nucleotide or cytosine nucleotide, $Q_1$ through $Q_n$ may be the same or different from one another and represent either an uracil nucleotide, adenine nucleotide, cytosine nucleotide or guanine nucleotide, $R_1$ through $R_n$ represent nucleotides that are respectively complementary to $Q_1$ through $Q_n$, $W_1$ through $W_4$ may be the same or different from one another and represent either an uracil nucleotide, adenine nucleotide cytosine nucleotide or guanine nucleotide, $X_1$ through $X_m$ may be the same or different from one another and represent either an uracil nucleotide, adenine nucleotide, cytosine nucleotide or guanine nucleotide, and m and n may be the same or different from each other and represent an integer from 1 to 10);

(13) a polyribonucleotide in general formula (V) set forth in (12) wherein S is an adenine nucleotide and n is 3;

(14) a process for cleaving polyribonucleotide ζ, which comprising the nucleotide sequence represented by general formula (VI), at the site indicated with the arrow in the formula using polyribonucleotide ε, which comprising the nucleotide sequence represented by the following general formula (VI):

wherein,

U represents an uracil nucleotide, C a cytosine nucleotide, A an adenine nucleotide, and G a guanine nucleotide, S represents either an adenine nucleotide or a cytosine nucleotide, $Q_1$ through $Q_n$ may be the same or different from one another and represent either an uracil nucleotide, adenine nucleotide, cytosine nucleotide or guanine nucleotide, $R_1$ through $R_n$ represent nucleotides that are respectively complementary to $Q_1$ through $Q_n$, $W_1$ through $W_4$ may be the same or different from one another and represent either an uracil nucleotide, adenine nucleotide, cytosine nucleotide or guanine nucleotide, $X_1$ through $X_m$ may be the same or different from one another and represent either an uracil nucleotide, adenine nucleotide, cytosine nucleotide or guanine nucleotide, P represents either an uracil nucleotide, adenine nucleotide, cytosine nucleotide or guanine nucleotide, L represents either an uracil nucleotide, adenine nucleotide or cytosine nucleotide, V represents either an adenine nucleotide in the case S is a cytosine nucleotide or an uracil or cytosine nucleotide in the case S is an adenine nucleotide, $Y_1$ through $Y_4$ represent nucleotides respectively complementary to $W_1$ through $W_4$, and $Z_1$ through $Z_m$ represent nucleotides respectively complementary to $X_1$ through $X_m$, m and n may be the same or different from each other and represent an integer from 1 to 10);

(15) a process for cleaving polyribonucleotide ζ in general formula (VI) set forth in (14), wherein L is an uracil nucleotide and V is a cytosine nucleotide, using polyribonucleotide ε, wherein S is an adenine nucleotide and n is 3;

(16) a DNA that codes for the polyribonucleotide set forth in (12) or (13);

(17) a recombinant vector that includes the DNA set forth in (16); and,

(18) a host cell tranfected with the recombinant vector set forth in (17).

The polyribonucleotide of the present invention has a high level of ribozyme activity (to be referred to as a "ribozyme polyribonucleotide"), and has the capacity to specifically cleave a polyribonucleotide having a predetermined sequence in a cell. Thus, in the case a polyribonucleotide that has a detrimental effect on the living body is present in a plant, animal or human, said polyribonucleotide can be specifically cleaved in the living body by using this ribozyme polyribonucleotide.

The DNA of the present invention codes for the ribozyme polyribonucleotide of the present invention, and has the capacity to specifically cleave a desired polyribonucleotide by incorporating it into a cell using a suitable vector. The target cell may be a plant, animal or human cell.

Preferable examples of the polyribonucleotide of the present invention include the polyribonucleotide set forth in (2), (4) or (13), and the polyribonucleotide set forth in (4) or (13) are more preferred.

Optimum examples of the polyribonucleotide of the present invention consist of the following compounds (b) (SEQ ID NO: 1), (c)(SEQ ID NO: 2), (e)(SEQ ID NO: 4), (f)(SEQ ID NO: 5), (i)(SEQ ID NO: 7), (j)(SEQ ID NO: 8), (n)(SEQ ID NO: 9) and (q)(SEQ ID NO: 10).

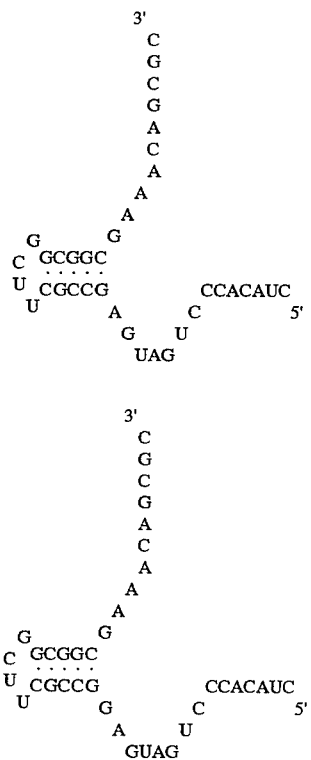

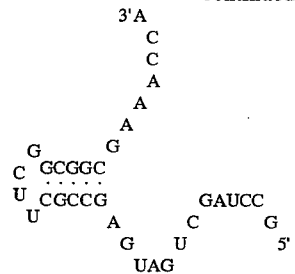

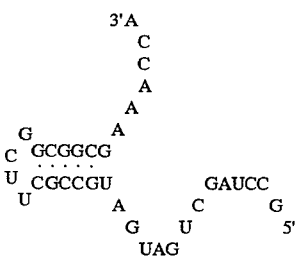

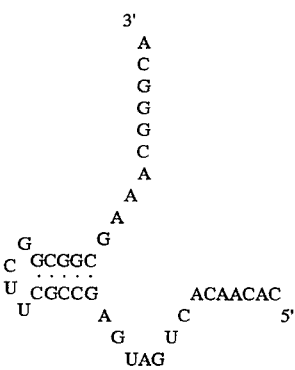

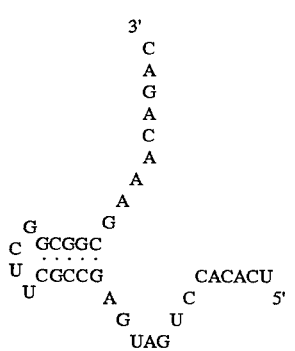

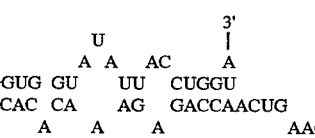

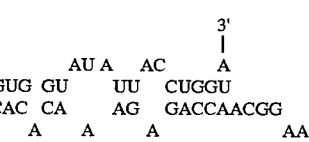

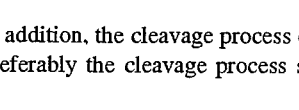

In addition, the cleavage process of the present invention is preferably the cleavage process set forth in (9), (11) or (15), with the cleavage process set forth in (11) or (15) being more preferred.

The compound of the present invention represented by the above-mentioned general formula (I), (II) or (V) can be used in the form of a salt. Examples of such salts include inorganic or organic salts including alkaline metals such as sodium and potassium: alkaline earth metals such as calcium: ammonia: basic amino acids such as lysine and arginine: and alkyl amines such as triethylamine.

The polyribonucleotide of the present invention can be synthesized using a nucleoside 3'-O-phosphoramidites purchased from American Bionetics, Inc., wherein the 2'-hydroxyl group is protected with a tert-butyldimethylsilyl group and the 5'-hydroxyl group is protected with a dimethoxytrityl group, with the DNA/RNA automatic synthesizer manufactured by Applied Biosystem, Inc. (Proc. Natl. Acad. Sci. USA, 85, 5764–5768, (1988)).

Removal of the β-cyanoethyl group attached to the phosphate acid group, severing of the polyribonucleotide chain from the carrier, and removal of the acyl group of the base portion were carried out by treatment with base, the protecting group for the 2'-hydroxyl group was removed by treatment with tetrabutylammonium fluoride, and the protecting group for the 5'-hydroxyl group was removed by treatment with acid. By performing subsequent purification with purification procedures normally used in purification of nucleic acids, examples of which include desalting and various types of chromatography such as reverse phase and ion exchange chromatography (including high-performance liquid chromatography), the compound represented by the above-mentioned general formula (I), (II) or (V) can be obtained.

In vitro cleavage reaction of a substrate polyribonucleotide chain by ribozyme polyribonucleotide can be carried out by the procedure described below (JIKKEN IGAKU, 8, 1685–1689, (1990)).

The 5' terminal of the polyribonucleotide used as the substrate is labeled with a radioisotope and so forth. Ribozyme polyribonucleotide is then added to this labeled polyribonucleotide in a buffer containing magnesium chloride, followed by warming.

The reaction temperature is preferably 0° to 100° C., and more preferably 30° to 50° C.

After a predetermined period of time, the reaction is stopped by adding EDTA to the reaction solution, and the solution is subjected to homochromatography. The cleavage rate can be calculated by quantitatively determining the cleavage products with the Fuji Bioimage Analyzer BAS 2000 System.

A DNA chain that codes for ribozyme polyribonucleotide can be synthesized using the DNA automatic synthesizer manufactured by Applied Biosystems, Inc. Determination of the sequence of the resulting DNA can be performed by using, for example, the Maxam-Gilbert Chemical modification method (Maxam, A. M. and Gilbert, W. (1980): "Methods in Enzymology" 65, 499–559) or the dideoxynucleotide chain termination method using an M13 phage (Messing, J. and Vieira, J. (1982): Gene 19, 269–276).

In addition, this DNA chain can be formed into a double strand chain by annealing, and an expression vector can be constructed by ligating said double strand DNA under the control of a promoter that acts intracellularly using DNA ligase.

The host cell of the present invention can be obtained by introducing this expression vector into a host cell. In addition, the expression vector of the present invention can simultaneously be mass produced.

Examples of host cells are as follows.

Examples of host cells of procaryotic cells include *Escherichia coli, Bacillus subtilis* and so forth. In order to express the target gene within the host cell, the host cell should be transfected with a replicon originating in a strain able to adapt to the host cell, namely a plasmid vector containing a replication origin and a regulating sequence. In addition, it is preferable that the vector has a sequence that is able to give selectivity of transformation (phenotype) to the transfected cell.

For example, in the case of *E. coli*, the *E. coli* K12 strain and so forth are frequently used. Although pBR322 and pUC type plasmids are typically used for the vector, the present invention is not limited to the use of these, and any known bacterial strains and vectors can be used.

Examples of promoters in the case of *E. coli* include tryptophan (trp) promoter, lactose (lac) promoter, tryptophan-lactose (tac) promoter, lipoprotein (lpp) promoter, lamda (λ) PL promoters of bacteriophage origin, and polypeptide chain elongation factor Tu (tufB) promoter and so forth. Any of these promoters can be used for production of the ribozyme polyribonucleotide of the present invention.

Although preferable examples of *Bacillus subtilis* include the 207–25 strain, while vectors such as pTUB228 (Ohmura K., et al., (1984), J. Biochem., 95, 87–93) are used, the present invention is not limited to these.

An example of a promoter that is frequently used is the regulating sequence of the α-amylase gene of *Bacillus subtilis*.

The cells of vertebrates, insects, yeasts and so forth are included in the host cells of eucaryotic organisms. Examples of vertebrate cells that are frequently used include the mouse cell NIH-3T3 (J. Virol., 4, 549–553, (1969)), the monkey cell cos (Gluzman Y., (1981), Cell, 23, 175–182), the dihydrofolate reductase-deletion strain of Chinese hamster ovary cells (CHO) (Urlaub, G. and Chasin, L. A. (1980), Proc. Natl. Acad. Sci. USA, 77, 4216–4220) and so forth. The present invention, however, is not limited to these.

Examples of expression vectors of vertebrate cells, that can be used normally include those having a promoter located upstream from the gene to be expressed, RNA splicing site, polyadenylated site and transcription terminal sequence and so forth. These may also have a replication origin as necessary. An example of said expression vector is pSV2dhfr and so forth having an SV40 initial promoter (Subramani, S. et al. (1981), Mol. Cell. Biol., 1, 854–864), but the present invention is not limited to this.

In addition, yeast can also be used as eucaryotes. Examples of expression vectors that can be used for eucaryotes such as said yeasts include the promoter of the alcohol dehydrogenase gene (Bennetzen, J. and Hall, B. D., (1982), J. Biol. Chem., 257, 3018–3025) and the promoter of the acid phosphatase gene (Miyanohara, A. et al. (1983), Proc. Natl. Acad. Sci. USA, 80, 1–5) and so forth.

Other procaryotic or eucaryotic host cells can be transformed by introducing a vector obtained in the manner described above. Moreover, genes can be expressed in the respective host cells by introducing a suitable promoter and sequence involved in transformation into these vectors.

In the case where *E. coli* is used as the host cell, for example, vectors that can be used as the expression vector are those having a pBR322 replication origin, enable autonomous proliferation in *E. coli*, and which are equipped with a transcriptional promoter and translational starting signal. Said expression vector can be incorporated in *E. coli* by the calcium chloride method (Mandel M. and A. Higa, J.

Mol. Biol., 53,154, (1970)), the method of Hanahan (Hanahan D. and M. Meselson, Gene, 10, 63, (1980)), electroporation (Neumann E. et al., (1982) EMBO J., 1, 841–845) and so forth, thus enabling a cell to be obtained that has been transfected by the desired vector.

Cells transfected with the desired vector obtained as described above can be cultured in accordance with conventional methods, and the desired ribozyme polyribonucleotide can be produced within the cells by said culturing. Various types of media routinely used corresponding to the host cells being employed can be suitably selected as the medium used in said culturing. Examples of media that can be used in the case of the above-mentioned E. coli include tryprone-yeast medium (1.6% Bactotryptone, 1.0% yeast extract and 10.5% NaCl (pH 7.0)) and peptone medium (Difco) and so forth.

In addition, in the case where the COS cell is used, for example, vectors that can be used as the expression vector are those having an SV40 replication origin, enable autonomous proliferation in COS cells and which are equipped with a transcriptional promoter, transcriptional terminating signal and RNA splicing site. Said expression vector can be incorporated in COS cells by the DEAE-dextran method (Luthman, H. and Magnusson, G. (1983) Nucleic Acids Res. 11, 1295–1308), the calcium phosphate-DNA coprecipitation method (Graham, F. L. and van der Ed, A. J. (1973) Virology 52, 456–457), electroporation (Neumann E. et al., (1982) EMBO J., 1, 841–845) and so forth, thus enabling a cell to be obtained that has been transfected by the desired vector.

In addition, in the case of using CHO cells as the host cell, by co-tranfecting with an expression vector and a vector able to express a neo-gene that functions as a G418-resistant marker, examples of which include pRSVneo (Sambrook, J. et al. (1989): "Molecular Cloning—A Laboratory Manual", Cold Spring Harbor Laboratory, New York), pSV2-neo (Southern, P. J. and Berg, P. (1982) J. Mol. Appl. Genet. 1, 327–341) and so forth, and then selecting G418-resistant colonies, transfected cells can be obtained that stably produce the ribozyme polyribonucleotide of the present invention.

Cells transfected with the desired vector obtained as described above can be cultured in accordance with conventional methods, and ribozyme polyribonucleotide can be produced within the cells by said culturing. Various types of media routinely used corresponding to the host cells being employed can be suitably selected for the medium used in said culturing. Examples of media that can be used in the case of the above-mentioned COS cells include that to which serum components such as fetal bovine serum (FBS) have been added as necessary to media such as RPMI-1640 medium and Dulbecco's modified Eagle's minimum essential medium (DMEM).

The present invention also relates to a process for specifically cleaving a substrate polyribonucleotide using a ribozyme polyribonucleotide. Polyribonucleotide that has a detrimental effect on the living body can be specifically cleaved by carrying out the process of the present invention in the living body.

BRIEF DESCRIPTION OF THE DRAWINGS

FIG. 3 is a nucleotide sequence chart of a double-strand ribozyme polyribonucleotide gene (upper sequence is SEQ ID NO: 18 and lower sequence is SEQ ID NO: 19).

BEST MODE FOR CARRYING OUT THE INVENTION

Figure 1:
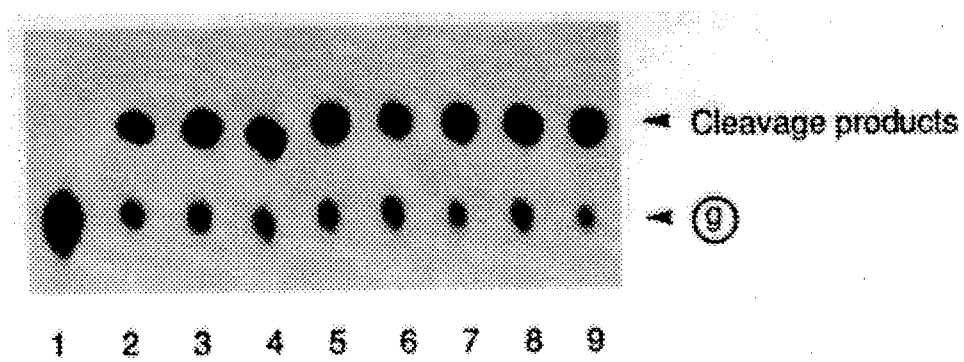
FIG. 1 is an analytical diagram of the substrate polyribonucleotide cleavage reaction by homochromatography.

The present invention will be described below in more detail by way of examples and reference examples, but the present invention is not limited to these.

EXAMPLE 1

Synthesis of Polyribonucleotide

The following polyribonucleotides (b), (c), (e) and (f) were synthesized by a DNA automatic synthesizer (ABI, Model 394 DNA/RNA Synthesizer) using nucleoside 3'-phosphoroamidites wherein the 5'-hydroxyl group is protected with a dimethoxytrityl group and the 2'-hydroxyl group is protected with a tert-butyldimethylsilyl group (purchased from American Bionetics Inc.).

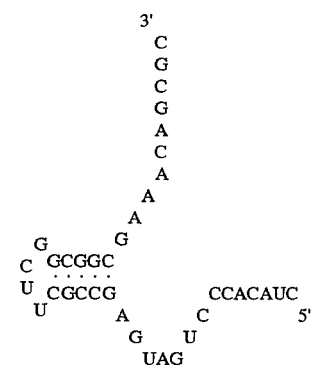

(b) (SEQ ID NO:1)

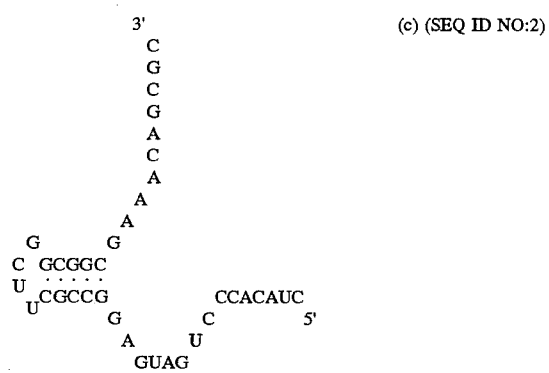

(c) (SEQ ID NO:2)

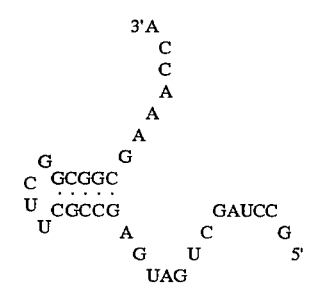

(e) (SEQ ID NO:4)

-continued

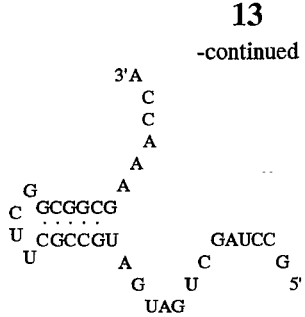
(f) (SEQ ID NO:5)

The RNA fragment was synthesized on a 1 μmol scale.

After completion of the synthesis, a CPG (controlled pore glass) to which the synthesized oligonucleotide was coupled, was treated at room temperature for 1 hour with a mixed solution of concentrated ammonia water and ethanol (3:1 v/v). After distilling off the solvent, 5 ml of ethanolic saturated ammonia was added, followed by warming at 55° C. for 16 hours. The solvent was distilled off and 1 ml of a solution of 1M TBAF (tetrabutylammonium fluoride) in THF (tetrahydrofuran) was added to the remaining solution, followed by stirring at room temperature for 24 hours. After 5 ml of 0.1M triethylammonium acetate (pH 7.0) was added to the mixture, C18 silica gel (Waters) column chromatography was performed (column size: 0.7×15 cm; eluted according to concentration gradient using a solvent of 5 to 40% $CH_3CN$ and 50 mM triethylammonium bicarbonate). Fractions having the coloring of dimethoxytrityl that eluted with $CH_3CN$ at a concentration of about 30% were collected, following by the addition of 5 ml of 0.01N HCl and stirring for 1 hour. After the mixture was neutralized with 0.1N aqueous ammonia, the aqueous layer was washed with ethyl acetate. After distilling off the solvent, the residue was dissolved in 1.2 ml of sterile water. The polyribonucleotides contained in this fraction were separated and purified with reverse phase HPLC and ion exchange HPLC.

Reverse phase HPLC was performed using an Inertsil ODS-2 column (φ10×250 mm, GL Sciences, Inc.) by the linear concentration gradient method using 0.1M triethylammonium acetate containing 5% $CH_3CN$ (pH 7.0) for solution A and 0.1M triethylammonium acetate containing 25% $CH_3CN$ (pH 7.0) for solution B.

In addition, ion exchange HPLC was performed using a TSK gel DEAE 2SW column (φ4.6×250 mm, Tosoh Co., Ltd.) by the linear concentration gradient method using 20% $CH_3CN/H_2O$ for solution A and 2M $HCOONH_4$ solution containing 20% $CH_3CN$ for solution B. The percentages of solution B used for reverse phase HPLC and ion exchange HPLC elution and retention times are shown in Table 1 below for each polyribonucleotide.

Reference Example 1

Synthesis of Polyribonucleotide

The following polyribonucleotides (a) and (d) (SEQ ID NO: 3) were synthesized, separated and purified according to the method described in Example 1.

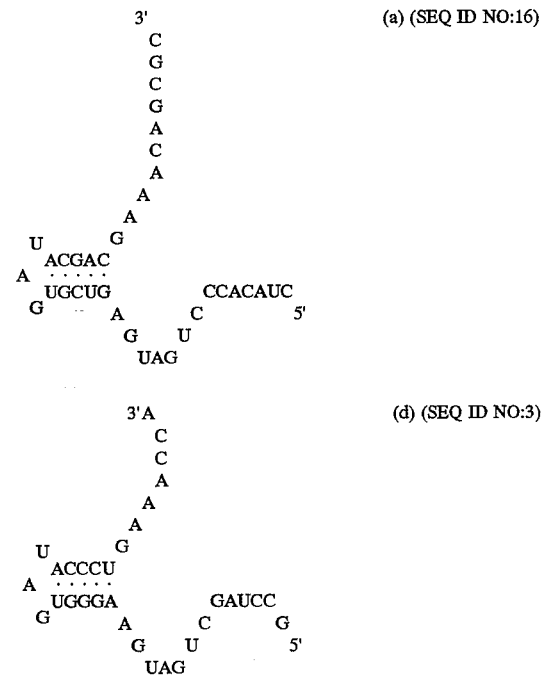

These polyribonucleotides were used in the control experiment described later as polyribonucleotides having low ribozyme activity.

In addition, the following polyribonucleotides (g) and (h)(SEQ ID NO: 6) were synthesized, separated and purified according to the method described in Example 1.

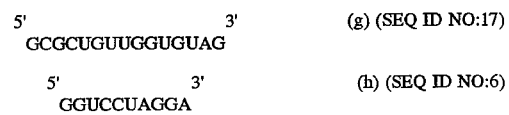

These polyribonucleotides were used in an experiment described later as substrates of a ribozyme cleavage reaction.

The percentages of solution B used for reverse phase HPLC and ion exchange HPLC elution and retention times are shown in Table 2 for each polyribonucleotide.

TABLE 1

| | B% | Total time of linear concentration gradient | Retention time |
|---|---|---|---|
| Reverse Phase HPLC | | | |
| (b) | 15% → 35% | (20 minutes) | 24.6 minutes |
| (c) | 10% → 50% | (20 minutes) | 21.4 minutes |
| (e) | 25% → 50% | (20 minutes) | 15.7 minutes |
| (f) | 25% → 45% | (20 minutes) | 16.5 minutes |
| Ion Exchange HPLC | | | |
| (b) | 30% → 50% | (20 minutes) | 12.4 minutes |
| (c) | 30% → 50% | (20 minutes) | 12.7 minutes |
| (e) | 30% → 50% | (20 minutes) | 12.9 minutes |
| (f) | 30% → 50% | (20 minutes) | 13.4 minutes |

TABLE 2

| | B% | Total time of linear concentration gradient | Retention time |
|---|---|---|---|
| Reverse Phase HPLC | | | |
| (a) | (Reverse phase HPLC was not performed) | | — |
| (g) | 10% → 40% | (20 minutes) | 19.0 minutes |
| (d) | 25% → 50% | (20 minutes) | 14.0 minutes |
| (h) | 10% → 35% | (20 minutes) | 18.7 minutes |
| Ion Exchange HPLC | | | |
| (a) | 20% → 50% | (30 minutes) | 22.5 minutes |
| (g) | 20% → 40% | (20 minutes) | 17.8 minutes |
| (d) | 30% → 50% | (20 minutes) | 15.0 minutes |
| (f) | 20% → 40% | (20 minutes) | 16.3 minutes |

EXAMPLE 2

Labeling of 5' Terminal of Substrate RNA

[γ-³²P]ATP (0.5 μl, 5 μci), a buffer (1 μl, 250 mM Tris-HCl (pH 7.6), 50 mM magnesium chloride, 50 mM mercaptoethanol), T4 polynucleotide kinase (0.5 μl, 1 unit, Takara Shuzo Co., Ltd.) and sterile water (3 μl) were added to either polyribonucleotide (g) or (h) described above (100 pmol) followed by incubating for 1 hour at 37° C. Unreacted [γ-³²P]ATP and salt were removed using NENSORB20 (Dupont Corporation). The residue was then dissolved in sterile water to obtain the 5'-labelled oligonucleotide.

EXAMPLE 3

Cleavage of Substrate Polynucleotide

The cleavage reaction of polyribonucleotide (a), polyribonucleotide (b) or polyribonucleotide (c) on polyribonucleotide (g) was carried out in the following manner.

Polyribonucleotide (g) labelled at its 5'-terminal was dissolved in a buffer (25 mM MgCl$_2$, 40 mM Tris-HCl (pH 7.5) and 20 mM NaCl). The ribozyme oligonucleotide was added to the solution to start the reaction so that the final concentration of substrate was 1 μM and the final concentration of ribozyme was 0.5 μM. After the mixture was warmed at 37° C. and a predetermined period of time elapsed, the reaction was stopped by mixing with EDTA, namely by sampling a portion of the reaction mixture so as to make the final concentration of EDTA 50 mM. The changes in substrate decomposition were then observed with passage of time. The cleavage products were separated by homochromatography and the cleavage rate was determined using a bioimage analyzer (Fuji Photo Film Co., Ltd.). The respective reaction forms are shown below.

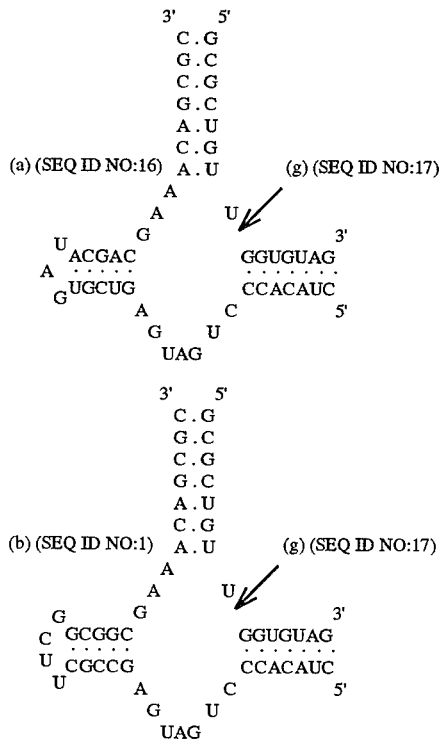

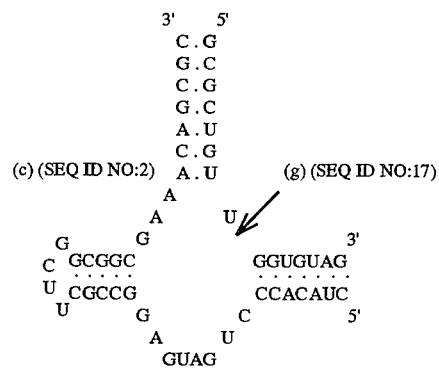

The results are shown in FIG. 1.

The polyribonucleotide having the oligonucleotide sequence of (g) has already been reported to be cleaved by (a) (Nucleic Acids Res. 17, 7059–7071 (1989)). Lane 1 in FIG. 1 represents (g) before the reaction. Lanes 2 through 5 represent the products of cleavage of (g) by (a), while lanes 6 through 9 represent the products of cleavage of (g) by (b). The cleavage products are respectively shown for 15, 30, 60 and 90 minutes after the start of the reaction. Due to the short chain length of the cleaved fragments, they are developed more quickly than the uncleaved (g) in homochromatography. In FIG. 1, these are shown at a location above the location of the uncleaved (g). In addition, (a) and (b) catalytically cleaved (g). The values for Km (Michaelis constant) and Kcat (reaction rate constant), which are used as parameters for this, were calculated using the Hanes-Woolf Plot. Those results are shown in Table 3.

TABLE 3

| Ribozyme | Km (μM) | Kcat (min⁻¹) | Kcat/Km (μM⁻¹min⁻¹) |
|---|---|---|---|
| (a) | 1.1 | 0.12 | 1.1 × 10⁻¹ (100)* |
| (b) | 0.63 | 0.08 | 1.3 × 10⁻¹ (118)* |

*Relative value when the ribozyme catalytic activity of (a) is taken to be 100.

As is shown in Table 3, the ribozyme wherein a thermodynamically stable 5'CUUCGG3' loop is introduced into the ribozyme polyribonucleotide sequence (b) demonstrates increased cleavage activity in comparison with that of (a).

In addition, the cleavage reaction of polyribonucleotide (d), polyribonucleotide (e) or polyribonucleotide (f) on polyribonucleotide (h) was also carried out in a buffer (25 mM MgCl$_2$, 40 mM Tris-HCl (pH 7.5) and 20 mM NaCl) so that the final concentration of substrate was 1 μM and the final concentration of ribozyme polyribonucleotide was 0.4 μM. The time in which half of the substrate was cleaved was then compared. The respective reaction forms were as shown below.

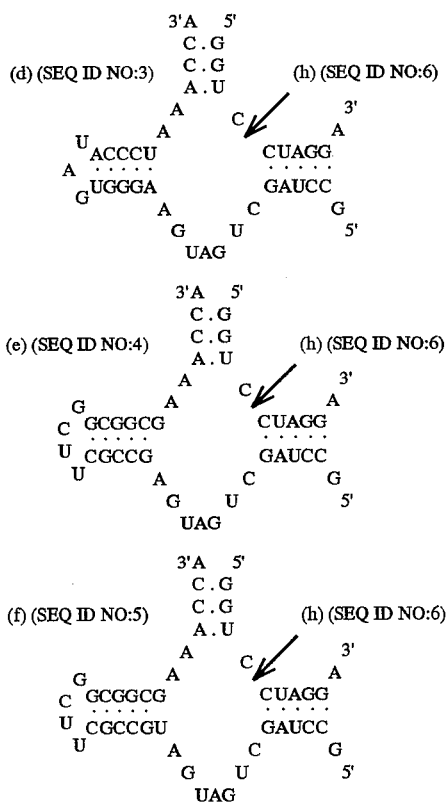

Those results are shown in Table 4.

TABLE 4

| Ribozyme | $t_{1/2}$(min) | Specific Activity |
|---|---|---|
| (d) | 21 | 1 |
| (e) | 7 | 3 |
| (f) | 15 | 1.4 |

Both (e) and (f) have thermodynamically stable loops in the form of 5'CUUCGG3', and their cleavage activities were higher than that of (d) which does not have a stable loop.

EXAMPLE 4

Construction of a Plasmid Having a Variant c-Ha-ras Gene wherein GGU of Codon 12 of Normal c-Ha-ras Gene is Changed to GUU (pRSV-rv12neo), and a Plasmid Having a Double-Strand DNA that Codes for a Ribozyme Polyribonucleotide that Cleaves Variant ras mRNA (pRZ4Δneo)

Point mutation of either of codons 12, 13 or 61 occurs in c-Ha-ras gene detected from human cancer (Nature (1982) 300, 143–149). When this variant c-Ha-ras gene is transfected into NIH3T3 cells, it is known that the variant c-Ha-ras gene is expressed and the cells are transformed (Nature (1982) 300, 143–149). It is thought that by cleaving the mRNA of an ras gene, wherein GGU of codon 12 of a normal c-Ha-ras gene is changed to GUU (Jpn. J. Cancer Res. (1989) 80, 200–203), using a ribozyme polyribonucleotide, expression of the variant ras gene in the NIH3T3 cells can be suppressed. The following provides a description of the construction of plasmid pRSV-rv12neo, having an ras gene wherein GGU of codon 12 of a normal c-Ha-ras gene is changed to GUU, and plasmid pRZ4Δneo, having a gene that codes for a ribozyme polyribonucleotide that cleaves that ras mRNA.

Figure 2:
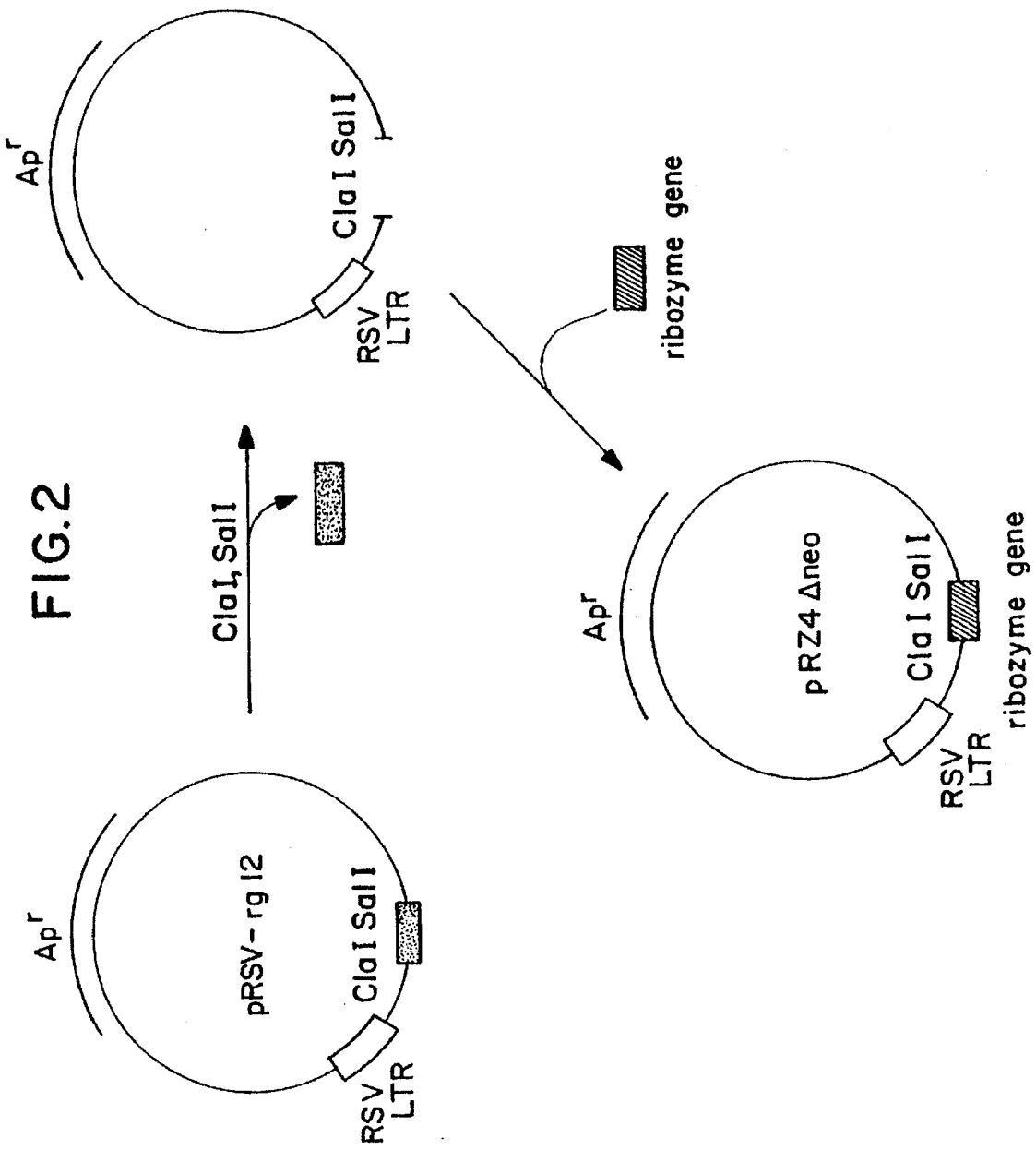
FIG. 2 is a diagram showing the construction of the plasmid pRZ4Δneo.

FIG. 2 indicates a summary of construction of pRZ4Δneo. 3 μg of pRSV-rg12 (Jpn. J. Cancer Res. (1989) 80, 200–20) was digested by warming overnight at 37° C. with ClaI (15 U, Takara Shuzo Co., Ltd.) and SalI (30 U, Takara Shuzo Co., Ltd.). After ethanol precipitation, the digestion product was dissolved in 0.1M Tris-HCl (pH 8.0, 48 μl), followed by addition of alkaline phosphatase derived from E. Coli (0.7 U, Takara Shuzo Co., Ltd.) and warming at 37° C. for 2 hours. After the mixture was treated with phenol-chloroform, a digestion product was obtained by ethanol precipitation. A ribozyme polyribonucleotide gene fragment formed into two strands by annealing (the base sequence is shown in FIG. 3, 0.2 pmol, 1 μl), a reaction buffer (4 μl, 330 mM Tris-HCl (pH 7.6), 33 mM $MgCl_2$), 0.2M 2-mercaptoethanol (1 μl) and T4 DNA ligase (1 μl, 350 U, Takara Shuzo Co., Ltd.) were added to the ClaI and SalI digestion products of pRSV-rg12 (1.5 μg, 0.5 pmol, 8 μl), followed by warming at 20° C. for 1.5 hours and precipitation with ethanol to obtain pRZ4Δneo.

The resulting pRZ4ΔΔneo was transfected into E. coli HB101 strain treated with $Ca^{2+}$ and cultured overnight in agar media containing ampicillin. Screening was the performed by rapid boiling method (Anal. Biochem. (1981) 114, 193–197) to isolate E. coli having pRZ4Δneo. This E. coli was then cultured and the pRZ4Δneo was isolated and purified according to the method of Norgard (Anal. Biochem. (1981) 113, 34–42).

Figure 4:
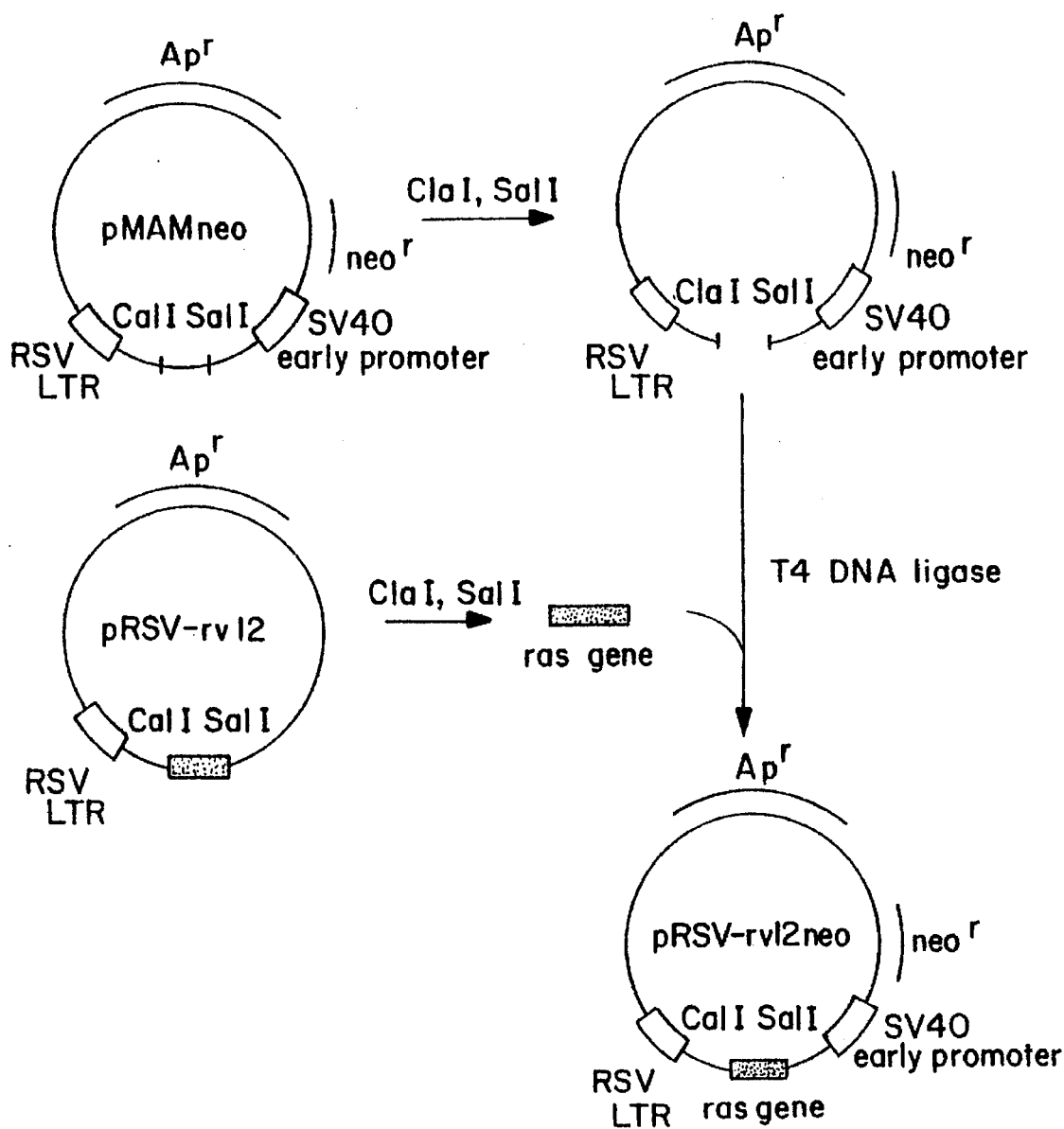
FIG. 4 is a diagram showing the construction of plasmid pRSV-rv12neo.

FIG. 4 indicates a summary of the construction of pRSV-rv12neo. pMAMneo (3 μg, Clontech Corporation) was digested by warming overnight at 37° C. with ClaI (10 U, Takara Shuzo Co., Ltd.) and SalI (20 U, Takara Shuzo Co., Ltd.). The mixture was dissolved in 0.1M Tris-HCl (pH 8.0, 48 μl) and to the resulting solution was added alkaline phosphatase derived from E. Coli (0.7U, Takara Shuzo Co., Ltd.), followed by warming at 37° C. for 2 hours. After the mixture was treated with phenol-chloroform, a digestion product was obtained by ethanol precipitation. pRSV-rv12 (Jpn. J. Cancer Res. (1989) 80, 200–203) was similarly digested with ClaI and SalI, and then the variant c-Ha-ras gene fragment was separated by low-melting point agarose gel electrophoresis. The pMAMneo ClaI and SalI digestion products along with the variant c-Ha-ras gene fragment were ligated with T4 DNA ligase to obtain pRSV-rv12neo. This was then isolated and purified by a method similar to that used for isolating pRZ4Δneo.

EXAMPLE 5

Introduction of pRSV-rv12neo and pRZ4Δneo into NIH3T3 Cells by Co-Transfection and Isolation of Cells Exhibiting Morphology Identical to Normal Cells NIH3T3 cells transfected with pRSV-rv12neo having a variant c-Ha-ras gene, in which GGU of codon 12 of a normal c-Ha-ras gene is changed to GUU, are known to be transformed. It is thought that the transcription product of the ras gene can be cleaved to return the transformed cells to a form identical to normal cells by expressing a gene that codes for ribozyme polyribonucleotide. The process will be described below.

pRSV-rv12neo (10 ng), pRZ4Δneo (2 μg) and NIH3T3 cell DNA as carrier DNA (30 μg) were transfected into NIH3T3 cells ($8\times10^5$ cells) by the calcium phosphate method (Virology (1973) 52, 456–457). Two days later, the cells were cultured for about 1 week in DMEM media (containing 5% bovine serum) to which Geneticin (300 mg/500 ml, Gilbco Corporation) had been added. Those colonies that exhibited morphology identical to that of normal cells were detected microscopically. Those colonies were isolated using penicillin caps.

The introduction of pRSV-rv12neo into NIH3T3 cells has been confirmed by the PCR method (Science (1989) 239, 487–491). The following two primers were synthesized with the model 394 DNA/RNA automatic synthesizer of the ABI Corporation to be used. Namely, these consisted of an upper primer (CGATATGACCGAATACAAACT) (SEQ ID NO: 20) and a lower primer (TCGAGTATCAGCCTGGGCCA-GATTCGTCCGGCGGGTTAGCT)(SEQ ID NO: 21). Incidentally, the literature of Miura et al. (Jpn. J. Cancer Res. (1986) 77, 45–51) was referred to for the nucleotide sequences of the primers used here.

EXAMPLE 6

Confirmation of Ribozyme Effect by Northern Hybridization

After culturing the cells exhibiting identical morphology to normal cells isolated using the process of Example 5 in DMEM medium, the cells were collected by centrifugation and treated with RNAzol (Cinna Biotech Corporation) containing guanidinium thiocyanate to extract total RNA.

The total RNA obtained from the cells (approximately 20 μg) was applied to 1% agarose gel electrophoresis containing formaldehyde. This was transferred to a nitrocellulose filter and baked at 80° C. for 2 hours under reduced pressure to fix the RNA. The filter was immersed in 20 ml of pre-hybridization solution (5× SSC, 2× Denhardt, 1% SDS, 100 mg/ml salmon sperm DNA, 50 mM sodium phosphate (pH 6.7), 50% formamide) and shaken at 42° C. for 8 hours. c-Ha-ras gene, in which codon 12 had changed to GUU, was labeled by a random primed DNA labeling kit (Boehringer-Mannheim GmbH.), and this labeled form was added as a probe (1.1×10⁹ dpm/μg) to 10 ml of the above solution followed by shaking at 42° C. for 17 hours. After washing the filter with a solution of 0.2× SSC-0.5% SDS at 60° C., it was then analyzed with a bioimage analyzer (Fuji Photo Film Co., Ltd.). Human β-actin mRNA was used for the internal standard.

NIH3T3 cells transformed only with pRSV-rv12neo were selected for use as the positive control cells that express the variant c-Ha-ras gene. In addition, normal NIH3T3 cells were selected for use as the negative control cells that do not retain the variant c-Ha-ras gene. Total RNA was extracted from both types of cells using a similar process as that described above to attempt hybridization.

Figure 5:
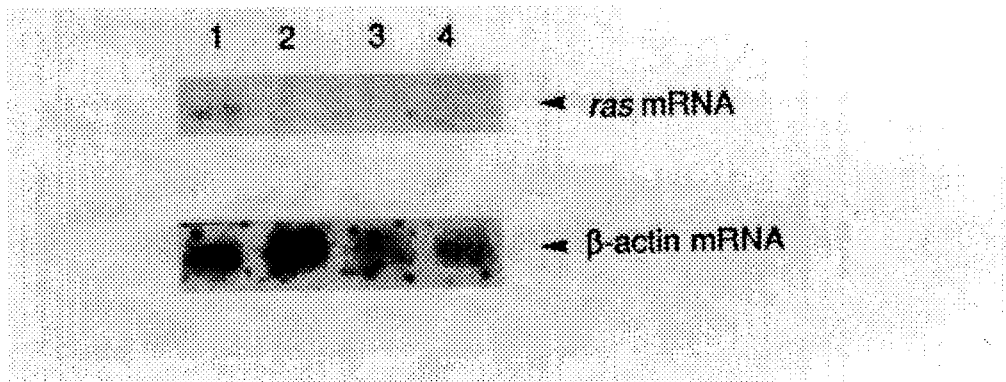
FIG. 5 is an analytical diagram of northern hybridization of NIH3T3 cells co-transfected with plasmids pRZ4Δneo and pRSV-rv12neo.

FIG. 5 indicates the results of northern hybridization. Lane 1 is the mRNA derived from NIH3T3 cells transformed with variant ras gene (pRSV-rv12neo). Lane 2 is the mRNA derived from normal NIH3T3 cells. Lanes 3 and 4 show the results of analysis of mRNA derived from colonies of cells co-transfected with pRZ4Δneo and pRSV-rv12neo that exhibited morphology identical to normal cells. Since ras mRNA was not able to be detected in lanes 3 and 4, ribozyme polyribonucleotide was thought to have cleaved that ras mRNA within the cells. This finding indicates that ribozyme polyribonucleotide suppresses the transformation of cells caused by expression of a variant ras gene.

EXAMPLE 7

Synthesis of Polyribonucleotide that Cleaves Substrate Polyribonucleotide Having a Base Sequence of Human Immunodeficiency Virus (HIV) RNA The following polyribonucleotides (i) and (j), which cleave a substrate polyribonucleotide having an HIV RNA base sequence, were synthesized by a DNA automatic synthesizer (Cyclon Plus DNA/RNA Synthesizer, Japan Millipore Limited) using nucleoside 3'-phosphoramidites (Japan Millipore Limited) wherein the 5'-hydroxyl group is protected with a dimethoxytrityl group and the 2'-hydroxyl group is protected with a tert-butyldimethylsilyl group.

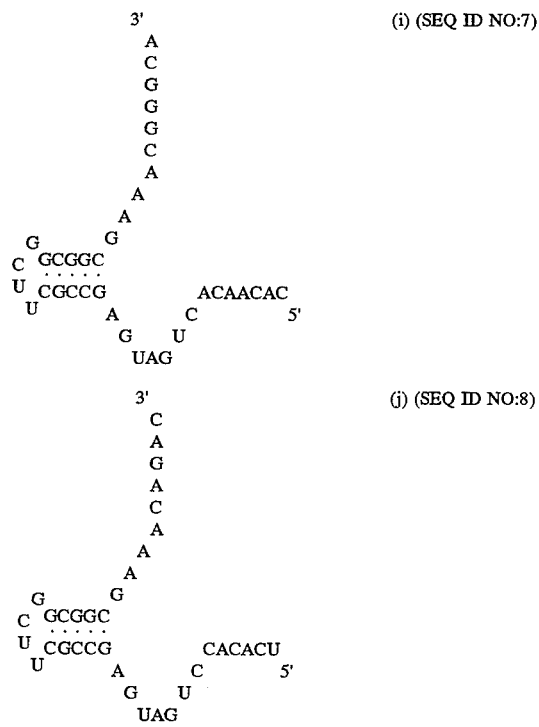

The RNA fragment was synthesized on a 1 μmol scale.

After completion of synthesis, a CPG (controlled pore glass), to which the synthesized oligonucleotide was coupled, was treated at room temperature for 2 hours with a mixed solution of concentrated ammonia water and ethanol (3:1 v/v), followed by warming at 55° C. for 16 hours. The solvent was distilled off and 1 ml of a 1M solution of TBAF (tetrabutylammonium fluoride) in THF (tetrahydrofuran) was added to the residue followed by stirring at room temperature for 24 hours. After 5 ml of 0.1M triethylammonium acetate (pH 7.0) was added to the mixture, C18 silica gel (Waters) column chromatography was performed (column size: 1.5×12 cm; eluted according to concentration gradient using a solvent of 20–40% CH₃CN and 50 mM triethylammonium bicarbonate). Fractions having the coloring of dimethoxytrityl that eluted with CH₃CN at a concentration of about 30% were collected, followed by the addition of 5 ml of 0.01N HCl and stirring for 1 hour. After neutralizing with 0.1N aqueous ammonia, the aqueous layer was washed with ethyl acetate. After distilling off the solvent, the product was dissolved in 3 ml of sterile water. The polyribonucleotides contained in this fraction were separated and purified with ion exchange HPLC.

Ion exchange HPLC was performed using a TSK gel DEAE 2SW colum (φ4.6×250 mm, Tosoh Co., Ltd.) by the linear concentration gradient method using 20% CH₃CN/H₂O for solution A and 2M HCOONH₄ aqueous containing 20% CH₃CN for solution B. The percentages of solution B used for the ion exchange HPLC elution and retention times are shown in Table 5 below for each polyribonucleotide.

TABLE 5

| B % | Total Time of Linear Concentration Gradient | Retention |
|---|---|---|
| (i): 20% → 60% | 20 minutes | 18.6 minutes |
| (j): 20% → 60% | 20 minutes | 17.9 minutes |

Reference Example 2

Synthesis of Polyribonucleotide Having an HIV RNA Base Sequence

Polyribonucleotide (k), having an HIV RNA base sequence (19 mer having sequences from nucleotide no. 106 to no. 124 described in the literature: Nature 313, 450–458 (1985)), polyribonucleotide (1) (10 mer having sequences from nucleotide no. 115 to no. 124 described in the above-mentioned literature) and polyribonucleotide (m) (6 mer having sequences from nucleotide no. 119 to no. 124 described in the above-mentioned literature) were synthesized, separated and purified according to the method described in Example 7.

| | |
|---|---|
| 5' GUGCCCGUCUGUUGUGUGA 3' | (k) (SEQ ID NO:22) |
| 5' UGUUGUGUGA 3' | (l) (SEQ ID NO:23) |
| 5' GUGUGA 3' | (m) (SEQ ID NO:24) |

Polyribonucleotide (k) was used in an experiment described hereinafter as the substrate for a ribozyme cleavage reaction. In addition, polyribonucleotides (1) and (m) were used in an experiment described hereinafter as controls for compounds produced in a ribozyme cleavage reaction. The percentages of solution B used for ion exchange HPLC elution and retention times are shown in Table 6 for each polyribonucleotide.

TABLE 6

| B % | Total Time of Linear Concentration Gradient | Retention |
|---|---|---|
| (k): 10% → 60% | 20 minutes | 19.1 minutes |
| (l): 10% → 60% | 20 minutes | 17.1 minutes |
| (m): 10% → 60% | 20 minutes | 15.1 minutes |

EXAMPLE 8

Cleavage of Polyribonucleotide Having an HIV RNA Base Sequence by a Polyribonucleotide Having Ribozyme Activity The cleavage reactions of polyribonucleotide (i) on polyribonucleotide (k), and of polyribonucleotide (j) on polyribonucleotide (k) were carried out as described below.

Substrate polyribonucleotide (k) was dissolved in a buffer (25 mM $MgCl_2$, 40 mM Tris-HCl (pH 7.5) and 20 mM NaCl). The ribozyme polyribonucleotide was added to start the reaction so that the final concentration of substrate was 1.25 μM and the final concentration of ribozyme was 0.063 μM. After the mixture was warmed at 37° C. for 1 hour, the cleavage reaction was analyzed by ion exchange HPLC (TSK gel DEAE 2SW, 4.6×250 mm, 20% $CH_3CN/H_2O$ for solution A, 2M aqueous $HCOONH_4$ containing 20% $CH_3CN$ for solution B: linear concentration gradient of 10→60%/20 minutes, flow rate: 1 ml/min). The respective reaction forms are shown below.

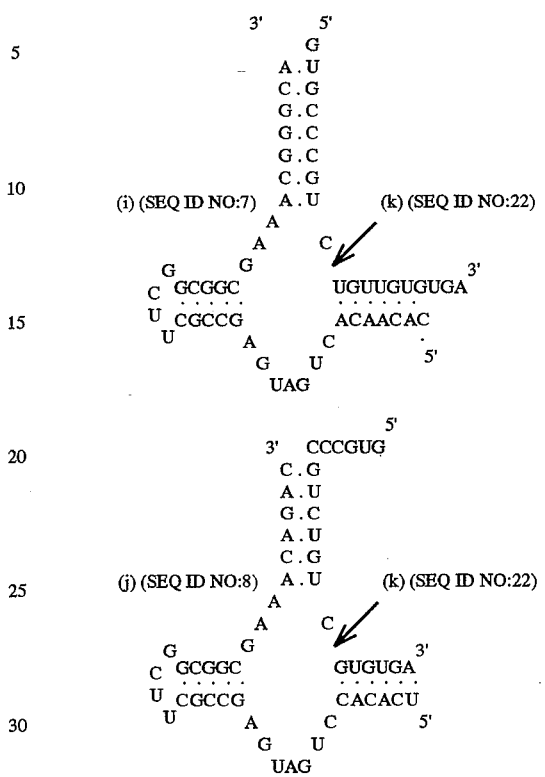

In the case of reacting polyribonucleotide (i) on polyribonucleotide (k) under the above-mentioned conditions, a decrease was observed in the peak of polyribonucleotide (k) in ion exchange HPLC. In contrast, two peaks appeared at 17.1 minutes and 17.3 minutes. Since the peak having a retention time of 17.1 minutes coincided with the retention time of polyribonucleotide (1), it was confirmed that cleavage took place at the target location. In addition, determination of the cleavage rate from the area value obtained from HPLC of the peak of polyribonucleotide (k) after the cleavage reaction as well as the two peaks that appeared yielded a value of 90%.

In the case of reacting polyribonucleotide (j) on polyribonucleotide (k) under the above-mentioned conditions, a decrease was observed in the peak of polyribonucleotide (k) in ion exchange HPLC. In contrast, two peaks appeared at 15.1 minutes and 18.2 minutes. Since the peak having a retention time of 15.1 minutes coincided with the retention time of polyribonucleotide (m), it was confirmed that cleavage took place at the target location. In addition, determination of the cleavage rate from the area value obtained from HPLC of the peak of polyribonucleotide (k) after the cleavage reaction as well as the two peaks that appeared yielded a value of 88%.

EXAMPLE 9

Synthesis of Polyribonucleotide

The following polyribonucleotide (n) was synthesized by a DNA automatic synthesizer (Model 394 DNA/RNA Synthesizer, Applied Biosystems, Inc.) using nucleoside 3'-phosphoramidites wherein the 5'-hydroxyl group is protected with a dimethoxytrityls group and the 2'-hydroxyl group is protected with a tert-butyldimethylsilyl group (purchased from American Biotics, Inc.).

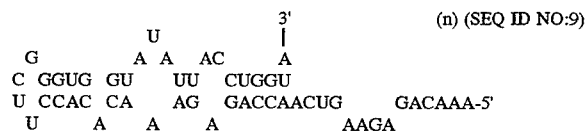

(n) (SEQ ID NO:9)

The RNA fragment was synthesized on a 1 μmol scale.

After completion of synthesis, a CPG (controlled pore glass), to which the synthesized oligonucleotide was coupled, was treated at room temperature for 1 hour with a mixed solution of concentrated ammonia water and ethanol (3:1 v/v). After the solvent was distilled off, 5 ml of ethanolic saturated ammonia was added to the residue, followed by warming at 55° C. for 16 hours. The solvent was distilled off and 1 ml of a 1M solution of TBAF (tetrabutylammonium fluoride) in THF (tetrahydrofuran) was added to the remaining solution followed by stirring at room temperature for 24 hours. After 5 ml of 0.1M triethylammonium acetate (pH 7.0) was then added to the mixture, C18 silica gel (Waters) column chromatography was performed (column size: 0.7×15 cm; eluted according to concentration gradient using a solvent of 5 to 40% $CH_3CN$ and 50 mM triethylammonium bicarbonate). Fractions having the coloring of dimethoxytrityl that eluted with $CH_3CN$ at a concentration of about 30% were collected, followed by the addition of 5 ml of 0.01N HCl and stirring for 1 hour. After the mixture was neutralized with 0.1N aqueous ammonia, the aqueous layer was washed with ethyl acetate. After the solvent was distilled off, the residue was dissolved in 1.2 ml of sterile water. The polyribonucleotides contained in this fraction were separated and purified with reverse phase HPLC and ion exchange HPLC.

The reverse phase HPLC was performed using an Inertsil ODS-2 column (φ10×250 mm, GL Sciences Inc.) by the linear concentration gradient method using 0.1M triethylammonium acetate containing 5% $CH_3CN$ (pH 7.0) for solution A and 0.1M triethylammonium acetate containing 25% $CH_3CN$ (pH 7.0) for solution B.

In addition, the ion exchange HPLC was performed using a TSK gel DEAE 2SW column (φ4.6×250 mm, Tosoh Co., Ltd.) by the linear concentration gradient method using 20% $CH_3CN/H_2O$ for solution A and 2M $HCOONH_4$ containing 20% $CH_3CN$ for solution B. The percentages of solution B used for the reverse phase HPLC and the ion exchange HPLC elution and retention times are shown in Table 7 below for polyribonucleotide (n).

TABLE 7

| Type of Analysis | B % | Total Time of Linear Concentration Gradient | Retention Time |
|---|---|---|---|
| Reverse phase HPLC | 10% → 50% | 20 minutes | 18.1 minutes |
| Ion exchange HPLC | 30% → 50% | 20 minutes | 20.0 minutes |

In addition, the following polyribonucleotides (o) and (p) have already been reported by Sekiguchi et al. (Nucleic Acids Res. 19, 6833–6838 (1991)).

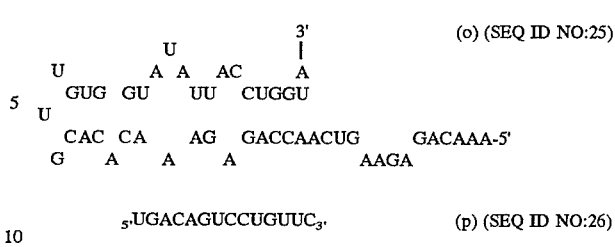

$_5$UGACAGUCCUGUUC$_3$.   (p) (SEQ ID NO:26)

EXAMPLE 10

Labeling of 5' Terminal of Substrate Polyribonucleotide (P)

[γ-$^{32}$P]ATP (0.5 μl, 5 μci), a buffer (1 μl, 250 mM Tris-HCl (pH 7.6), 50 mM magnesium chloride, 50 mM 2-mercaptoethanol), T4 polyribonucleotide kinase (0.5 μl, 1 unit, Takara Shuzo Co., Ltd.) and sterile water (3 μl) were added to the above-mentioned polyribonucleotide (p) (100 pmol) followed by incubating at 37° C. for 1 hour. Unreacted [γ-$^{32}$P]ATP and salt were removed using NENSORB20 (Dupont Corporation). The residue was then dissolved in sterile water to obtain the 5'-labelled oligonucleotide.

EXAMPLE 11

Cleavage of Substrate Polyribonucleotide

The cleavage reaction of polyribonucleotide (n) or (o) on substrate polyribonucleotide (p) was carried out in the following manner.

Polyribonucleotide (p) (1.62 pmol) labelled at its 5'-terminal was dissolved in 10 μl of a buffer (40 mM Tris-HCl (pH 7.5), 12 mM $MgCl_2$ and 2 mM spermidine 3 HCl). In addition, after ribozyme polyribonucleotide (n) or (o) (0.64 pmol) was dissolved in 10 μl of the same buffer, each solution was warmed at 65° C. for 2 minutes, followed by cooling with water. The ribozyme solutions were then added to the substrate to start the reaction.

After a predetermined period of time had elapsed, the reaction was stopped by sampling 2 μl of the reaction solution in a solution containing 2 μl of 50 mM EDTA. The changes in substrate decomposition were then observed with passage of time. The cleavage products were separated by homochromatography and the cleavage rate was determined using a bioimage analyzer (BAS2000 System, Fuji Photo Film Co., Ltd.). The respective reaction forms are shown below.

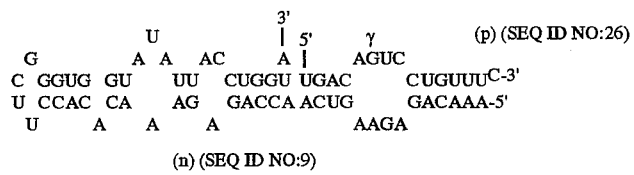

(n) (SEQ ID NO:9)

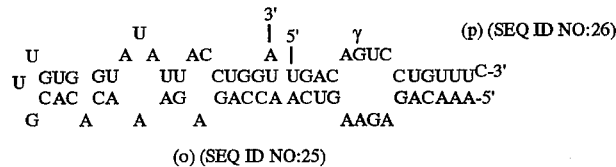

(o) (SEQ ID NO:25)

Figure 6:
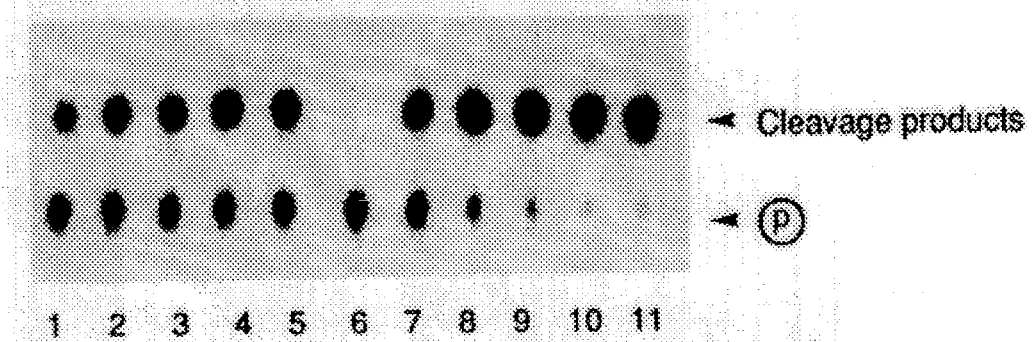
FIG. 6 is an analytical diagram of a substrate polyribonucleotide by homochromatography.

The results in the case of a reaction temperature of 42° C. are shown in FIG. 6.

It has already been reported that polyribonucleotide (p) is cleaved by polyribonucleotide (o) having a naturally-occurring base sequence (Nucleic Acids Res. 19, 6833–6838 (1991)).

In FIG. 6, lane X6 indicates (p) before reaction. Lanes 1 through 5 are the products of cleavage of (p) by (o), while lanes 7 through 11 are the products of cleavage of (p) by (n). The cleavage products are respectively shown for 3, 9, 12, 15 and 18 minutes after the start of the reaction.

Due to the short chain length of the cleaved fragments, they are developed more quickly than the uncleaved (p) in homochromatography. In FIG. 6, the cleaved fragments are shown at a higher position than the uncleaved (p).

In addition, the time in which half of substrate (P) is cleaved by either (n) or (o) (t½) was determined. Those results are shown in Table 8 together with those for cleavage reaction at 32°, 37° and 47° C.

TABLE 8

| Temperature (°C.) | t½when using (n) (minutes) | t½when using (o) (minutes) |
|---|---|---|
| 32 | 15 | 24 |
| 37 | 4 | 8 |
| 42 | 2 | 10 |
| 47 | 8 | 54 |

As shown in Table 8, a ribozyme polyribonucleotide (n), in which a 5'CUUCGG3' thermodynamically stable loop is introduced into its sequence, demonstrated increased cleavage activity at temperatures from 32° C. to 47° C. in comparison with the naturally-occuring form (o).

EXAMPLE 12

Synthesis of Polyribonucleotide (q) that Cleaves Substrate Polyribonucleotide Having the Base Sequence of Human Immunodeficiency Virus (HIV) RNA The following polyribonucleotide (q), which cleaves a substrate polyribonucleotide having an HIV RNA base sequence, was synthesized by a DNA automatic synthesizer (Cyclone Plus DNA/RNA Synthesizer, Japan Millipore Limited) using nucleoside 3'-phosphoramidites (Japan Millipore Limited) wherein the 5'-hydroxyl group is protected with a dimethoxytrityl group and the 2'-hydroxyl group is protected with a tert-butyldimethylsilyl group.

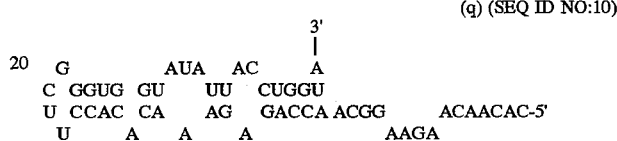

The RNA fragment was synthesized on a 1 µmol scale.

After completion of synthesis, a CPG (controlled pore glass), to which the synthesized oligonucleotide was coupled, was treated at room temperature for 2 hours with a mixture of concentrated ammonia water and ethanol (3:1 v/v), followed by warming at 55° C. for 16 hours. The solvent was distilled off and 1 ml of a 1M solution of TBAF (tetrabutylammonium fluoride) in THF (tetrahydrofuran) was added to the residue followed by stirring at room temperature for 24 hours. After then adding 5 ml of 0.1M triethylammonium acetate (pH 7.0), C18 silica gel (Waters) column chromatography was performed (column size: 1.5× 12 cm; eluted according to concentration gradient using 20 to 40% $CH_3CN$ and an aqueous 50 mM triethylammonium bicarbonate as a solvent). Fractions having the coloring of dimethoxytrityl that eluted with $CH_3CN$ at a concentration of about 30% were collected, followed by the addition of 5 ml of 0.01 N HCl and stirring for 1 hour. After the mixture was neutralized with 0.1N aqueous ammonia, the aqueous layer was washed with ethyl acetate. After distilling off the solvent, the product was dissolved in 3 ml of sterile water. The polyribonucleotides contained in this fraction were separated with ion exchange HPLC, and then additionally separated and purified with reverse phase HPLC.

The ion exchange HPLC was performed using a TSK gel DEAE 2SW column (4.6×250 mm, Tosoh Co., Ltd.) by the linear concentration gradient method using 20% $CH_3CN$/ $H_2O$ for solution A and an aqueous 2M $HCOONH_4$ containing 20% $CH_3CN$ for solution B (B 20%-→60% (20 minutes)). Polyribonucleotide (q) eluted at 20.6 minutes.

The reverse phase HPLC was performed using an Inertsil ODS column (6.0×150 mm, GL Sciences Inc.) by the linear concentration gradient method using 0.1M triethylammonium acetate (TEAA, pH 7.0) containing 5% $CH_3CN$ for solution A and 0.1M TEAA containing 25% $CH_3CN$ (pH 7.0) for solution B (B 20%-→60% (20 minutes)). Polyribonucleotide (q) eluted at 18.2 minutes.

Reference Example 3

Synthesis of Polyribonucleotide Having an HIV RNA Base Sequence

Polyribonucleotide (r), having an HIV RNA base sequence (19 mer having sequences from nucleotide no. 106 to no. 124 described in the literature: Nature 313, 450–458

(1985)), and polyribonucleotide (s) (13 mer having sequences from nucleotide no. 112 to no. 124 described in the above-mentioned literature) were synthesized, separated and purified according to the method described in Example 12.

5'GUGOCCGUCUGUUGUGUGA3'  (r)(SEQ ID NO: 22)

5'GUCUGUUGUGUGA3'  (s)(SEQ ID NO: 27)

Polyribonucleotide (r) was used in an experiment described hereinafter as the substrate for a hairpin ribozyme cleavage reaction. In addition, polyribonucleotide (s) was used in an experiment described hereinafter as a compound formed in a ribozyme cleavage reaction.

The percentages of solution B used for ion exchange HPLC elution and retention times, along with the percentages of solution B used for reverse phase HPLC elution and retention times are shown in Table 9 for each polyribonucleotide (r) and (s).

TABLE 9

| Type of Analysis | B % | Total Time of Linear Concentration Gradient | Retention Time |
|---|---|---|---|
| (r) Reverse phase HPLC | 10% → 50% | 20 minutes | 14.8 minutes |
| Ion exchange HPLC | 10% → 60% | 20 minutes | 19.1 minutes |
| (s) Reverse phase HPLC | 10% → 50% | 20 minutes | 12.2 minutes |
| Ion exchange HPLC | Ion exchange HPLC was not performed. | | |

EXAMPLE 13

Cleavage of Polyribonucleotide Having an HIV RNA Base Sequence by a Polyribonucleotide Having Ribozyme Activity The cleavage reaction of polyribonucleotide (q) on polyribonucleotide (r) was carried out as described below.

Substrate polyribonucleotide (r) (250 pmol) was dissolved in 100 µl of a buffer (40 mM Tris-HCl (pH 7.5), 12 mM MgCl$_2$ and 2 mM Spermidine.3HCl). In addition, the ribozyme polyribonucleotide (q) (12.5 pmol) was dissolved in 100 µl of the same buffer. Both solutions were respectively warmed at 65° C. for 2 minutes followed by cooling with ice. The reaction was then started by adding the ribozyme solution to the substrate. After the mixture was warmed at 37° C. for 1 hour, the reaction was stopped by addition of 50 µl of 50 mM EDTA. The cleavage reaction was analyzed by reverse phase HPLC (Inertsil ODS, 6.0× 150 mm, linear concentration gradient method using 0.1M TEAA containing 5% CH$_3$CN (pH 7.0) for solution A and 0.1M TEAA containing 25% CH$_3$CN (pH 7.0) for solution B, B 10%—→50%/20 minutes, flow rate: 1 ml/min). The respective reaction forms are shown below.

In the case of reacting polyribonucleotide (q) on polyribonucleotide (r) under the above-mentioned conditions, a decrease was observed in the peak of polyribonucleotide (r) in reverse phase HPLC. In contrast, a peak appeared at 12.2 minutes. Since this peak coincided with the retention time of polyribonucleotide (s), it was confirmed that cleavage took place at the target location. In addition, determination of the cleavage rate from the area value obtained from HPLC of the peak of polyribonucleotide (r) after the cleavage reaction as well as the peak that appeared at 12.2 minutes yielded a value of 97%.

Industrial Applicability

The ribozyme polyribonucleotide of the present invention can be administered directly with a carrier that can be used pharmacologically in animals, plants and humans. Examples of its administration forms include oral administration in the form of tablets, capsules, granules, powders or syrups or parenteral administration in the form of injections, intravenous infusion or suppositories.

In addition, the ribozyme polyribonucleotide of the present invention can also be administered by enclosing in a transporter such as a liposome.

Although the dose varies according to symptoms, age, body weight and so forth, it is ordinary administered to an adult in an amount of about 0.1 mg to 1000 mg per day in the case of oral administration, and this dose may be given in a single administration or over the course of several separate administrations. In the case of parenteral administration, it is administered to an adult in an amount of 0.1 mg to 1000 mg per dosing, and this can be administered by subcutaneous injection, intramuscular injection or intravenous injection.

Further, the effect of the present invention can also be obtained by incorporating the DNA of the present invention into a suitable vector and administering said vector into the body to express the ribozyme polyribonucleotide in cells. Retrovirus and vaccinia virus are examples of such vectors.

Moreover, cells are isolated from the living body of an animal, plant or human, the said cells are transfected with the expression vector of the present invention, and the transfected cells are cultured to be given those cells the capacity to produce a desired ribozyme polyribonucleotide in those cells, followed by transplanting these transfected cells into the original donor body to impart resistance to the specific polyribonucleotide to the living body. The use of this process makes it possible to make the human body resistant to, for example, polyribonucleotides associated with a specific disease such as AIDS, or polyribonucleotides related to a cancer gene.

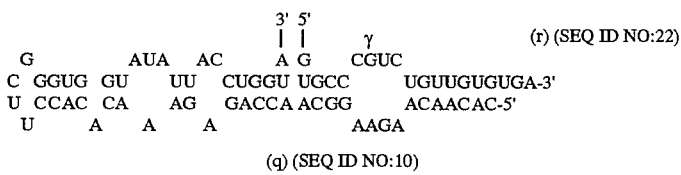

(q) (SEQ ID NO:10)

We claim:

1. A polyribonucleotide represented by the following formula (I):

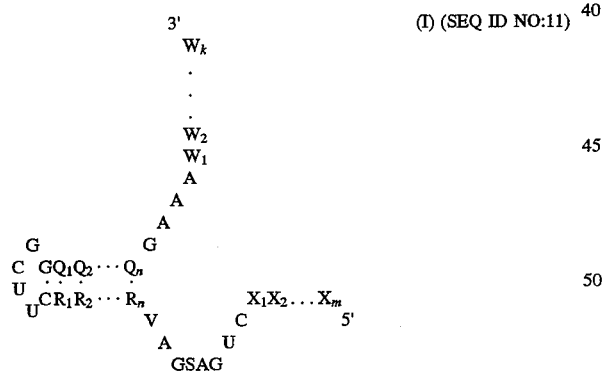

(I) (SEQ ID NO:11)

wherein,

U represents an uracil nucleotide, C a cytosine nucleotide, A an adenine nucleotide, and G a guanine nucleotide, S represents either an uracil nucleotide, adenine nucleotide, cytosine nucleotide or guanine nucleotide, V represents either an uracil nucleotide, adenine nucleotide, cytosine nucleotide or guanine nucleotide, $Q_1$ through $Q_n$ may be the same or different from one another and represent either a cytosine nucleotide or guanine nucleotide, $R_1$ through $R_n$ represent nucleotides that are respectively complementary to $Q_1$ through $Q_n$, $W_1$ through $W_k$ may be the same or different from one another and represent either an uracil nucleotide, adenine nucleotide, cytosine nucleotide or guanine nucleotide, $X_1$ through $X_m$ may be the same or different from one another and represent either an uracil nucleotide, adenine nucleotide, cytosine nucleotide or guanine nucleotide, and k, m and n may be the same or different from one another and represent an integer from 1 to 10.

2. The polyribonucleotide in the formula (I) according to claim 1, wherein $W_1$ is a cytosine nucleotide or a guanine nucleotide.

3. A polyribonucleotide represented by the following formula (II):

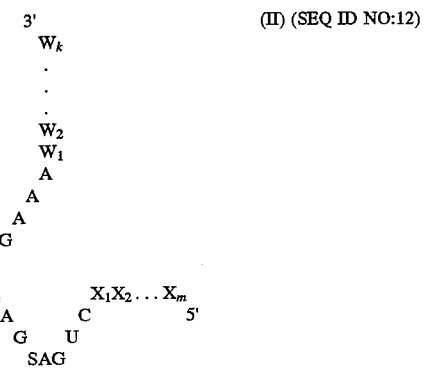

(II) (SEQ ID NO:12)

wherein,

U represents an uracil nucleotide, C a cytosine nucleotide, A an adenine nucleotide, and G a guanine nucleotide, S represents either an uracil nucleotide, adenine nucleotide, cytosine nucleotide or guanine nucleotide, $Q_1$ through $Q_n$ may be the same or different from one another and represent either a cytosine nucleotide or guanine nucleotide, $R_1$ through $R_n$ represent nucleotides that are respectively complementary to $Q_1$ through $Q_n$, $W_1$ through $W_k$ may be the same or different from one another and represent either an uracil nucleotide, adenine nucleotide, cytosine nucleotide or guanine nucleotide, $X_1$ through $X_m$ may be the same or different from one another and represent either an uracil nucleotide, adenine nucleotide, cytosine nucleotide or guanine nucleotide, and k, m and n may be the same or different from one another and represent an integer from 1 to 10.

4. The polyribonucleotide of the formula (II) according to claim 3, wherein $W_1$ is a cytosine nucleotide or a guanine nucleotide.

5. A DNA that codes for the polyribonucleotide according to claim 1, 2, 3 or 4.

6. A recombinant vector that includes the DNA according to claim 5.

7. A host cell transfected with the recombinant vector according to claim 6.

8. A process for cleaving a polyribonucleotide β(SEQ ID NO: 13) at a site indicated with an arrow in the following formula (III) comprising contacting a substrate polyribonucleotide β in the formula (III) with a ribozyme polyribonucleotide α (SEQ ID NO: 11) in the following formula (III):

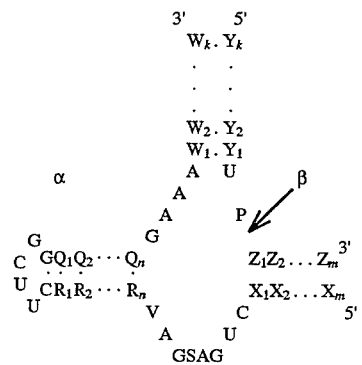

wherein,

U represents an uracil nucleotide, C a cytosine nucleotide, A an adenine nucleotide, and G a guanine nucleotide, S represents either an uracil nucleotide, adenine nucleotide, cytosine nucleotide or guanine nucleotide, V represents either an uracil nucleotide, adenine nucleotide, cytosine nucleotide or guanine nucleotide, $Q_1$ through $Q_n$ are the same or different from one another and represent either a cytosine nucleotide or guanine nucleotide, $R_1$ through $R_n$ represent nucleotides that are respectively complementary to $Q_1$ through $Q_n$, $W_1$ through $W_k$ are the same or different from one another and represent either an uracil nucleotide, adenine nucleotide, cytosine nucleotide or guanine nucleotide, $X_1$ through $X_m$ are the same or different from one another and represent either an uracil nucleotide, adenine nucleotide, cytosine nucleotide or guanine nucleotide, P represents either an uracil nucleotide, adenine nucleotide or cytosine nucleotide, $Y_1$ through $Y_k$ represent nucleotides that are respectively complementary to $W_1$ through $W_k$, $Z_1$ through $Z_m$ represent nucleotides that are respectively complementary to $X_1$ through $X_m$, and k, m and n are the same or different from one another and represent an integer from 1 to 10.

9. The process for cleaving the polyribonucleotide β in formula (III) according to claim 8, wherein $Y_1$ is a guanine nucleotide or cytosine nucleotide complementary to $W_1$, wherein $W_1$ is a cytosine nucleotide or guanine nucleotide.

10. A process for cleaving a polyribonucleotide δ (SEQ ID NO: 13) at a site indicated with an arrow in the following formula (IV) comprising contacting a substrate polyribonucleotide δ in the following formula (IV) with a ribozyme polyribonucleotide γ (SEQ ID NO: 12) in the following formula (IV):

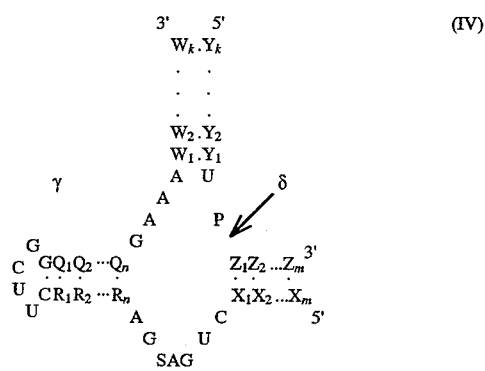

wherein,

U represents an uracil nucleotide, C a cytosine nucleotide, A an adenine nucleotide, and G a guanine nucleotide, S represents either an uracil nucleotide, adenine nucleotide, cytosine nucleotide or guanine nucleotide, $Q_1$ through $Q_n$ are the same or different from one another and represent either a cytosine nucleotide or guanine nucleotide, $R_1$ through $R_n$ represent nucleotides that are respectively complementary to $Q_1$ through $Q_n$, $W_1$ through $W_k$ are the same or different from one another and represent either an uracil nucleotide, adenine nucleotide, cytosine nucleotide or guanine nucleotide, $X_1$ through $X_m$ are the same or different from one another and represent either an uracil nucleotide, adenine nucleotide, cytosine nucleotide or guanine nucleotide, P represents either an uracil nucleotide, adenine nucleotide or cytosine nucleotide.

$Y_1$ through $Y_k$ represent nucleotide that are respectively complementary to $W_1$ through $W_k$, $Z_1$ through $Z_m$ represent nucleotides that are respectively complementary to $X_1$ through $X_m$, and k, m and n are the same or different from one another and represent an integer from 1 to 10.

11. The process for cleaving the polyribonucleotide δ (SEQ ID NO: 13) in formula (IV) according to claim 10, wherein $Y_1$ is a guanine nucleotide or cytosine nucleotide complementary to $W_1$, wherein $W_1$ is a cytosine nucleotide or guanine nucleotide.

12. A polyribonucleotide containing the nucleotide sequence represented by the following formula (V) (SEQ ID NO: 14):

```
                    3'
                    |
        G       AUA  AC      A                                            (V)
    C  GQ₁Q₂...Qₙ GU   UU   CUGGU
    U  CR₁R₂...Rₙ CA   AG   GACCAW₄W₃W₂W₁    X₁X₂...Xₘ-5'
        U       A    A   A              AAGS
``` wherein,

U represents an uracil nucleotide, C a cytosine nucleotide, A an adenine nucleotide, and G a guanine nucleotide, S represents either an adenine nucleotide or cytosine nucleotide, $Q_1$ through $Q_n$ may be the same or different from one another and represent either an uracil nucleotide, adenine nucleotide, cytosine nucleotide or guanine nucleotide, $R_1$ through $R_n$ represent nucleotides that are respectively complementary to $Q_1$ through $Q_n$, $W_1$ through $W_4$ may be the same or different from one another and represent either an uracil nucleotide, adenine nucleotide, cytosine nucleotide or guanine nucleotide, $X_1$ through $X_m$ may be the same or different from one another and represent either an uracil nucleotide, adenine nucleotide, cytosine nucleotide or guanine nucleotide, and m and n may be the same or different from each other and represent an integer from 1 to 10.

13. The polyribonucleotide in the formula (V) (SEQ ID NO: 14) according to claim 12, wherein S is an adenine nucleotide and n is 3.

14. A process for cleaving a polyribonucleotide ζ (SEQ ID NO: 15), which is included in the nucleotide sequence represented by a formula (VI), at a site indicated with an arrow in the formula (VI) comprising contacting a substrate polyribonucleotide in the following formula (VI) with a ribozyme polyribonucleotide ε (SEQ ID NO: 14), which is included in the nucleotide sequence represented by the following formula (VI):

```
                3'
                | 5'              γ                           (VI)
        G       AUA  AC      A |       PGLV        ζ
    C  GQ₁Q₂...Qₙ GU   UU   CUGGU Y₄ Y₃ Y₂ Y₁   Z₁Z₂...Zₘ-3'
    U  CR₁R₂...Rₙ CA   AG   GACCAW₄W₃W₂W₁       X₁X₂...Xₘ-5'
        U       A    A   A              AAGS
                                                  ε
``` wherein,

U represents an uracil nucleotide, C a cytosine nucleotide, A an adenine nucleotide, and G a quanine nucleotide, S represents either an adenine nucleotide or a cytosine nucleotide, $Q_1$ through $Q_n$ are the same or different from one another and represent either an uracil nucleotide, adenine nucleotide, cytosine nucleotide or guanine nucleotide, $R_1$ through $R_n$ represent nucleotides that are respectively complementary to $Q_1$ through $Q_n$, $W_1$ through $W_4$ are the same or different from one another and represent either an uracil nucleotide, adenine nucleotide, cytosine nucleotide or guanine nucleotide, $X_1$ through $X_m$ are the same or different from one another and represent either an uracil nucleotide, adenine nucleotide, cytosine nucleotide or guanine nucleotide, P represents either an uracil nucleotide, adenine nucleotide, cytosine nucleotide or guanine nucleotide, L represents either an uracil nucleotide, adenine nucleotide or cytosine nucleotide, V represents either an adenine nucleotide when S is a cytosine nucleotide or an uracil or cytosine nucleotide when S is an adenine nucleotide, $Y_1$ through $Y_4$ represent nucleotides that are respectively complementary to $W_1$ through $W_4$, $Z_1$ through $Z_m$ represent nucleotides that are respectively complementary to $X_1$ through $X_m$, and m and n are the same or different from each other and represent an integer from 1 to 10.

15. The process for cleaving the polyribonucleotide ζ in the formula (VI) according to claim 14, wherein L is an uracil nucleotide and V is a cytosine nucleotide, wherein S is an adenine nucleotide and n is 3.

16. A DNA that codes for the polyribonucleotide according to claim 12 or 13.

17. A recombinant vector that includes the DNA according to claim 16.

18. A host cell tranfected with the recombinant vector according to claim 17.

19. The polyribonucleotide according to claim 1, which is selected from the group consisting of

```
         3'                                     (SEQ ID NO: 1)
         C
         G
         C
         G
         A
         C
         A
         A
          A
      G       G
    C  GCGGC
    U  CGCCG              CCACAUC
       U     A       C         5',
              G     U
              UAG
```

```
         3'                                     (SEQ ID NO: 2)
         C
         G
         C
         G
         A
         C
         A
         A
          A
      G       G
    C  GCGGC
    U  CGCCG              CCACAUC
       U     G       C         5',
              A     U
              GUAG
```

```
         3'A                                    (SEQ ID NO: 4)
          C
          C
          A
          A
          A
      G       G
    C  GCGGC
    U  CGCCG              GAUCC
       U     A       C       G
              G     U        5',
              UAG
```

-continued
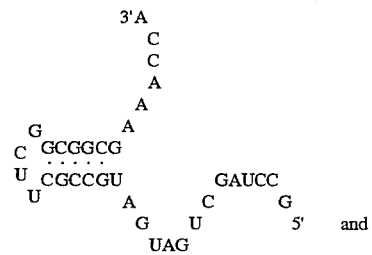
(SEQ ID NO: 5)
and
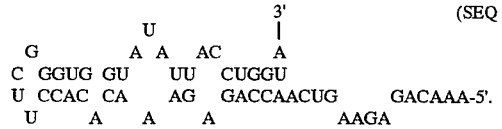
(SEQ ID NO: 9)
20. The polyribonucleotide of claim 1, which is
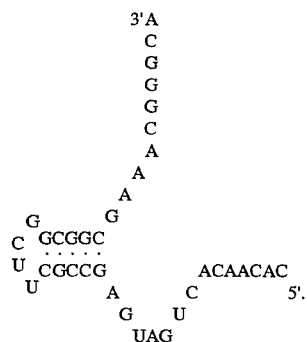
(SEQ ID NO: 7)
21. The polyribonucleotide of claim 1, which is
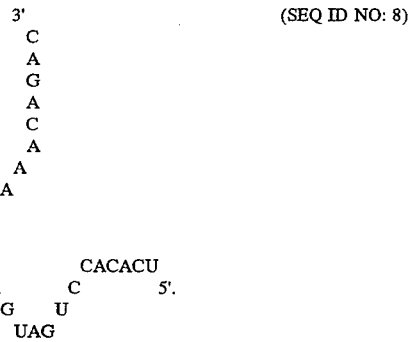
(SEQ ID NO: 8)
22. The polyribonucleotide according to claim 1, which is
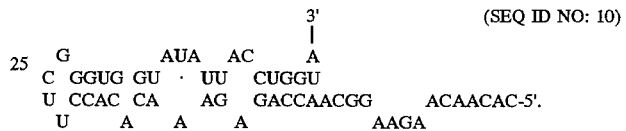
(SEQ ID NO: 10)
* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:1:

CUACACCCUG AUGAGCCGCU UCGGCGGCGA AACAGCGC            38

( 2 ) INFORMATION FOR SEQ ID NO:2:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:2:

CUACACCCUG AUGAGGCCGC UUCGGCGGCG AAACAGCGC           39

( 2 ) INFORMATION FOR SEQ ID NO:3:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:3:

GCCUAGCUGA UGAAGGGUGA UACCCUGAAA CCA                 33

( 2 ) INFORMATION FOR SEQ ID NO:4:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:4:

GCCUAGCUGA UGAGCCGCUU CGGCGGCGAA ACCA  34

( 2 ) INFORMATION FOR SEQ ID NO:5:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:5:

GCCUAGCUGA UGAUGCCGCU UCGGCGGCGA AACCA  35

( 2 ) INFORMATION FOR SEQ ID NO:6:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: mRNA ( i i i ) HYPOTHETICAL: N ( i v ) ANTI-SENSE: N ( x i ) SEQUENCE DESCRIPTION: SEQ ID NO:6:

GGUCCUAGGA  10

( 2 ) INFORMATION FOR SEQ ID NO:7:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:7:

CACAACACUG AUGAGCCGCU UCGGCGGCGA AACGGGCA  38

( 2 ) INFORMATION FOR SEQ ID NO:8:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:8:

UCACACCUGA UGAGCCGCUU CGGCGGCGAA ACAGAC  36

( 2 ) INFORMATION FOR SEQ ID NO:9:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:9:

AAACAGAGAA GUCAACCAGA GAAACACACC UUCGGGUGGU AUAUUACCUG GUA     53

( 2 ) INFORMATION FOR SEQ ID NO:10:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:10:

CACAACAAGA AGGCAACCAG AGAAACACAC CUUCGGGUGG UAUAUUACCU GGUA     54

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:11:

NNNCUGANGA NSSSCUUCGG SSSGAAANNN     30

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:12:

NNNCUGANGA SSSCUUCGGS SSGAAANNN     29

( 2 ) INFORMATION FOR SEQ ID NO:13:

( i ) SEQUENCE CHARACTERISTICS:
        ( A ) LENGTH: 8 base pairs ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: N ( i v ) ANTI-SENSE: N ( x i ) SEQUENCE DESCRIPTION: SEQ ID NO:13:

NNNUHNNN  8

( 2 ) INFORMATION FOR SEQ ID NO:14:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:14:

NNNMGAANNN NACCAGAGAA ACANNNCUUC GGNNNGUAUA UUACCGGUA  50

( 2 ) INFORMATION FOR SEQ ID NO:15:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: N ( i v ) ANTI-SENSE: N ( x i ) SEQUENCE DESCRIPTION: SEQ ID NO:15:

NNNNNGHHNN N  11

( 2 ) INFORMATION FOR SEQ ID NO:16:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: unknown ( i i ) MOLECULE TYPE: mRNA ( i i i ) HYPOTHETICAL: N ( i v ) ANTI-SENSE: N ( x i ) SEQUENCE DESCRIPTION: SEQ ID NO:16:

CUACACCCUG AUGAGUCGUG AUACGACGAA ACAGCGC  37

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: N ( i v ) ANTI-SENSE: N ( x i ) SEQUENCE DESCRIPTION: SEQ ID NO:17:

GCGCUGUUGG UGUAG                                                                                                         15

( 2 ) INFORMATION FOR SEQ ID NO:18:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( x i ) SEQUENCE DESCRIPTION: SEQ ID NO:18:

CGATCTACAC CCTGATGAGC CGCTTCGGCG GCGAAACAGC GCG                                                  43

( 2 ) INFORMATION FOR SEQ ID NO:19:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( x i ) SEQUENCE DESCRIPTION: SEQ ID NO:19:

TCGACGCGCT GTTTCGCCGC CGAAGCGGCT CATCAGGGTG TAGAT                                         45

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N ( i v ) ANTI-SENSE: N ( x i ) SEQUENCE DESCRIPTION: SEQ ID NO:20:

CGATATGACC GAATACAAAC T                                                                                         21

( 2 ) INFORMATION FOR SEQ ID NO:21:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: N (i v) ANTI-SENSE: N (x i) SEQUENCE DESCRIPTION: SEQ ID NO:21:

TCGAGTATCA GCCTGGGCCA GATTCGTCCG GCGGGTTAGC T 41

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: mRNA (i i i) HYPOTHETICAL: N (i v) ANTI-SENSE: N (x i) SEQUENCE DESCRIPTION: SEQ ID NO:22:

GUGCCCGUCU GUUGUGUGA 19

(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: mRNA (i i i) HYPOTHETICAL: N (i v) ANTI-SENSE: N (x i) SEQUENCE DESCRIPTION: SEQ ID NO:23:

UGUUGUGUGA 10

(2) INFORMATION FOR SEQ ID NO:24:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (i i) MOLECULE TYPE: mRNA (i i i) HYPOTHETICAL: N (i v) ANTI-SENSE: N (x i) SEQUENCE DESCRIPTION: SEQ ID NO:24:

GUGUGA 6

(2) INFORMATION FOR SEQ ID NO:25:

(i) SEQUENCE CHARACTERISTICS:
        (A) LENGTH: 50 base pairs
        (B) TYPE: nucleic acid
        (C) STRANDEDNESS: single
        (D) TOPOLOGY: unknown (i i) MOLECULE TYPE: mRNA (i i i) HYPOTHETICAL: N (i v) ANTI-SENSE: N (x i) SEQUENCE DESCRIPTION: SEQ ID NO:25:

AAACAGAGAA GUCAACCAGA GAAACACACG UUGUGGUAUA UUACCUGGUA    50

(2) INFORMATION FOR SEQ ID NO:26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: mRNA (iii) HYPOTHETICAL: N (iv) ANTI-SENSE: N (xi) SEQUENCE DESCRIPTION: SEQ ID NO:26:

UGACAGUCCU GUUUC    15

(2) INFORMATION FOR SEQ ID NO:27:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: mRNA (iii) HYPOTHETICAL: N (iv) ANTI-SENSE: N (xi) SEQUENCE DESCRIPTION: SEQ ID NO:27:

GUCUGUUGUG UGA    13